US009978802B2

(12) United States Patent
Mazzillo et al.

(10) Patent No.: US 9,978,802 B2
(45) Date of Patent: May 22, 2018

(54) MULTIBAND OPTOELECTRONIC DEVICE FOR COLORIMETRIC APPLICATIONS AND RELATED MANUFACTURING PROCESS

(71) Applicant: STMICROELECTRONICS S.R.L., Agrate Brianza (IT)

(72) Inventors: Massimo Cataldo Mazzillo, Corato (IT); Valeria Cinnera Martino, Valverde (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 0 days. days.

(21) Appl. No.: 15/346,578

(22) Filed: Nov. 8, 2016

(65) Prior Publication Data
US 2017/0365636 A1    Dec. 21, 2017

(30) Foreign Application Priority Data

Jun. 21, 2016 (IT) .................. 102016000064091

(51) Int. Cl.

| H01L 27/146 | (2006.01) |
|---|---|
| H01L 31/02 | (2006.01) |
| G01N 21/25 | (2006.01) |
| H01L 31/107 | (2006.01) |
| H01L 31/0224 | (2006.01) |

(52) U.S. Cl.
CPC ..... *H01L 27/14645* (2013.01); *G01N 21/251* (2013.01); *H01L 27/14607* (2013.01); *H01L 27/14689* (2013.01); *H01L 31/02027* (2013.01); *H01L 31/022408* (2013.01); *H01L 31/107* (2013.01)

(58) Field of Classification Search
CPC ......... H01L 27/14645; H01L 27/14607; H01L 27/14689; H01L 31/02027; H01L 31/022408; H01L 31/107; G01N 21/251
USPC .................................................. 257/432, 438
See application file for complete search history.

(56) References Cited

U.S. PATENT DOCUMENTS

2010/0148040 A1    6/2010   Sanfilippo et al.
2010/0271108 A1 * 10/2010   Sanfilippo ............. H01L 31/107
                                                                 327/502

(Continued)

OTHER PUBLICATIONS

Feruglio, et al., "A Review of the CMOS Buried Double Junction (BDJ) Photodetector and its Applications," *Sensors*, 8(10): 6566-6594, 2008.

(Continued)

*Primary Examiner* — Cuong Q Nguyen
*Assistant Examiner* — Tong-Ho Kim
(74) *Attorney, Agent, or Firm* — Seed IP Law Group LLP

(57) ABSTRACT

An optoelectronic device for detecting radiation, comprising a semiconductor body including: a cathode region delimited by a front surface, having a first conductivity type and including a bottom layer; an anode region having a second conductivity type, which extends in the cathode region starting from the front surface and forms a surface junction with the cathode region; and a buried region having the second conductivity type, which extends within the cathode region and forms a buried junction with the bottom layer. The cathode region further includes a buffer layer, which is arranged underneath the anode region and overlies, in direct contact, the bottom layer. The buffer layer has a doping level higher than the doping level of the bottom layer.

19 Claims, 15 Drawing Sheets

(56) References Cited

U.S. PATENT DOCUMENTS

2011/0241149 A1    10/2011  Mazzillo et al.
2013/0030763 A1*   1/2013   Mazzillo .................. G01J 1/44
                                                         702/179

OTHER PUBLICATIONS

Kulkarni, et al., "Integrated spectral-polarization imaging sensor with aluminum nanowire polarization filters," *Optics Express*, 20 (21): 22997-23012, 2012.

* cited by examiner

MULTIBAND OPTOELECTRONIC DEVICE FOR COLORIMETRIC APPLICATIONS AND RELATED MANUFACTURING PROCESS

BACKGROUND

Technical Field

The present disclosure relates to a multiband optoelectronic device for colorimetric applications and to the corresponding manufacturing process.

Description of the Related Art

As is known, colorimetry envisages decomposition of visible light into a set of primary colors, such as in particular red (R), green (G), and blue (B). In other words, unlike spectrometry, where the light is analyzed in very narrow wavelength ranges, colorimetry envisages averaging the information over rather wide spectral ranges. For these reasons, colorimetry is characterized by ease of implementation and standardization, as well as by low costs. Further, the signals available on the output of a generic colorimetric sensor, also referred to as "RGB sensor", are directly compatible with the response of the human eye and may hence be used directly in applications of an imaging type.

Today RGB sensors are available, each of which is formed by an array of cells, each cell comprising three identical and independent photosensors, each of which is designed to detect a respective primary color, thanks to the use of corresponding polymeric optical filters. Unfortunately, since each of the three photosensors occupies only a fraction of the respective cell, each RGB sensor has a small active area as compared to the respective overall dimensions. Further, the resins that form the polymeric optical filters are subject to ageing, with consequent reduction of transmittance. In addition, said RGB sensors suffer, during decoding of the signals generated thereby, from the so-called phenomenon of formation of Moiré fringes, which causes the appearance of undesirable artefacts.

RGB sensors of different types are each formed by single-PN-junction photodiodes, the junctions of which are biased at different voltages for varying the extensions of the corresponding depleted regions. Variation of thickness of a depleted region entails variation of the wavelength of the photons to which the photodiode is most sensitive, since photons having different wavelengths are absorbed at different depths. Unfortunately, RGB sensors based upon PN junctions do not enable satisfactory decoupling of the optical responses in the red, green, and blue, since the optical response at the highest wavelength is given by the superposition of the optical responses at lower wavelengths. For this reason, RGB sensors based upon PN junctions use electronic circuitries designed to implement algorithms that enable extraction of the correct values of radiation in the red, blue, and green.

BRIEF SUMMARY

One embodiment of the present disclosure is an optoelectronic device that enables the drawbacks of the known art to be overcome at least in part.

According to one embodiment of the disclosure, an optoelectronic device for detecting radiation comprises a semiconductor body including:

a cathode region delimited by a front surface of the semiconductor body and having a first conductivity type, said cathode region having a lower layer;

an anode region having a second conductivity type, which extends in the cathode region starting from the front surface and forms a shallow junction with the cathode region; and a first buried region having the second conductivity type, which extends within the cathode region and forms a first buried junction with said lower layer. The cathode region further comprises a first buffer layer, which is arranged underneath the anode region and overlies, in direct contact, the lower layer, the first buffer layer having a doping level higher than a doping level of the lower layer.

According to one embodiment of the disclosure, a process for manufacturing an optoelectronic device for detecting radiation includes:

forming a cathode region in a semiconductor body, the cathode region being delimited by a front surface of the semiconductor body, having a first conductivity type, and including a lower layer;

inside the cathode region, forming, starting from the front surface, an anode region having a second conductivity type, the anode region forming a shallow junction with the cathode region; and inside the cathode region, forming a first buried region having the second conductivity type, the first buried region forming a first buried junction with the lower layer. Forming the cathode region further comprises forming, underneath the anode region, a first buffer layer that overlies, and directly contacts, the lower layer, the first buffer layer having a doping level higher than a doping level of the bottom layer.

BRIEF DESCRIPTION OF THE SEVERAL VIEWS OF THE DRAWINGS

For a better understanding of the disclosure, embodiments thereof are now described, purely by way of non-limiting example and with reference to the attached drawings, wherein.

DETAILED DESCRIPTION

Figure 1:
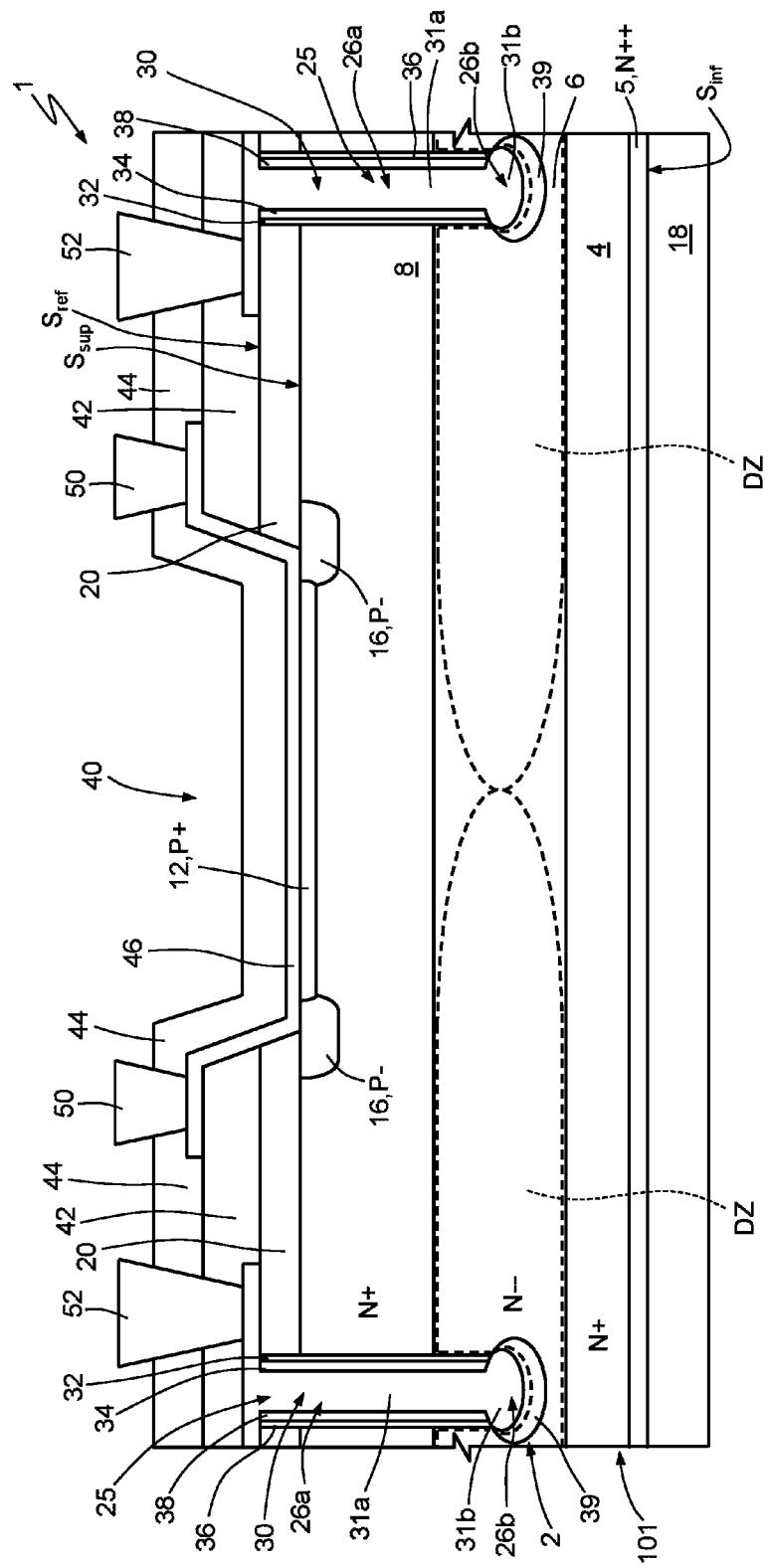
FIGS. 1-4 are schematic cross-sectional views of embodiments of the present optoelectronic device.

FIG. 1 shows an example of embodiment of an optoelectronic device 1, which is integrated in a semiconductor die 101. FIG. 1 and the subsequent figures are not in scale.

In detail, the optoelectronic device 1 comprises a semiconductor body 2, which is made, for example, of silicon and is delimited at the bottom and at the top, respectively, by a bottom surface $S_{inf}$ and a top surface $S_{sup}$.

The semiconductor body 2 includes a substrate 4 of an N+ type, which has a thickness of, for example, 350 µm; further, the substrate 4 is doped, for example, with phosphorus and has a doping level of, for example, $1 \cdot 10^{16}$ cm$^{-3}$. Without any loss of generality, in what follows it is assumed, where not expressly indicated, that the dopings of an N type are obtained using phosphorus as dopant.

The semiconductor body 2 further comprises a bottom enriched region 5, which extends underneath the substrate 4 and forms the bottom surface $S_{inf}$. Further, the bottom enriched region 5 is of an N++ type, has a thickness of, for example, 1 µm and has a doping level of, for example, $1 \cdot 10^{19}$ $cm^{-3}$.

The semiconductor body 2 further comprises a first epitaxial layer 6 and a second epitaxial layer 8, which in what follows will be referred to, respectively, as the "first lightly doped layer 6" and the "first heavily doped layer 8".

The first lightly doped layer 6 is arranged on the substrate 4, is of an N−− type, has a thickness of, for example, 15 µm and has a doping level of, for example, $5 \cdot 10^{13}$ $cm^{-3}$.

The first heavily doped layer 8 overlies, in direct contact, the first lightly doped layer 6, is of an N+ type, has a thickness of, for example, 10 µm and has a doping level of, for example, $5 \cdot 10^{17}$ $cm^{-3}$. The first heavily doped layer 8 forms the top surface $S_{sup}$.

An anode region 12, of a P+ type and having, in top plan view, a shape that is circular or polygonal (for example, quadrangular), extends in a top portion of the first heavily doped layer 8, starting from the top surface $S_{sup}$, without extending in a bottom portion of the first heavily doped layer 8, or in the first lightly doped layer 6. The anode region 12 is doped, for example, with boron, has a thickness comprised, for example, between 0.05 µm and 0.25 µm, and has a peak doping level of, for example, $5 \cdot 10^{18}$ $cm^{-3}$.

The optoelectronic device 1 further comprises a guard ring 16, which is of a P− type and extends only in the first heavily doped layer 8, starting from the top surface $S_{sup}$, for surrounding laterally the anode region 12, with which it is in direct contact. The guard ring 16 is doped, for example, with boron, has a thickness greater than the thickness of the anode region 12, and has a peak doping level of, for example, $1 \cdot 10^{18}$ $cm^{-3}$.

For practical purposes, the anode region 12, the first heavily doped layer 8, and the first lightly doped layer 6 form a PNI junction, since the electrical behavior of the first lightly doped layer 6 may be considered equivalent to that of an intrinsic layer. The first heavily doped layer 8 hence functions as cathode region. The PNI junction is designed to receive photons and to generate avalanche currents, as described in detail hereinafter.

In greater detail, the PNI junction is such that, straddling the interface between the anode region 12 and the first heavily doped layer 8, a depleted region is formed, which, thanks to the doping of the anode region 12, does not extend as far as the top surface $S_{sup}$, nor does it extend within the first lightly doped layer 6. Consequently, the PNI junction is characterized by a low breakdown voltage (of the order of one tenth of a volt). Further, the PNI junction forms a Geiger-mode avalanche photodiode (GM-APD), also known as single-photon avalanche diode (SPAD). For this purpose, as described in greater detail hereinafter, the PNI junction may be biased at a reverse voltage higher, in modulus, than the breakdown voltage. In this way, generation of a single electron-hole pair, following upon absorption of a photon incident on the optoelectronic device 1, is sufficient to trigger an ionization process that causes an avalanche multiplication of the carriers, with gains of around $10^6$ and consequent generation in short times (hundreds of picoseconds) of the avalanche current. The avalanche current may be appropriately collected, typically by an external circuitry connected to the PNI junction, and represents a first output signal of the optoelectronic device 1.

Since the anode region 12 has a particularly small thickness, the aforementioned Geiger-mode avalanche photodiode presents a high sensitivity in regard to radiation having a low wavelength (and hence in the blue), because the junction is very close to the top surface $S_{sup}$ and blue radiation has a low capacity of penetration into the semiconductor body 2. Further, the carriers generated inside the first lightly doped layer 6 or inside the non-depleted portion of the first heavily doped layer 8 present a low likelihood of reaching the depleted region and triggering the avalanche phenomenon, on account of the high doping level of the first heavily doped layer 8.

As regards the guard ring 16, it forms a PN diode with the first heavily doped layer 8 for preventing edge breakdown of the anode region 12.

Once again with reference to FIG. 1, the optoelectronic device 1 further comprises a bottom metallization 18, which extends in contact with the bottom enriched region 5, underneath the bottom surface $S_{inf}$, and is made, for example, of a multilayer structure including three layers (not shown) arranged in succession and made one of titanium, one of nickel, and one of gold.

The optoelectronic device 1 further comprises a dielectric region 20, which in what follows will be referred to as the first top dielectric region 20.

The first top dielectric region 20 extends over the top surface $S_{sup}$, in contact with the first heavily doped layer 8, and is made, for example, of TEOS oxide. Further, the first top dielectric region 20 is delimited at the top by a surface $S_{ref}$, which in what follows will be referred to as the "reference surface $S_{ref}$". In addition, the first top dielectric region 20 has a thickness of, for example, 1.6 µm.

The optoelectronic device 1 further comprises a first trench 25, which in top plan view has, for example, a ring shape, such as (to a first approximation) the shape of an annulus.

In detail, the first trench 25 extends through the first top dielectric region 20, starting from the reference surface $S_{ref}$, as well as through the first heavily doped layer 8 and a top portion of the first lightly doped layer 6. For example, the first trench 25 has a depth of 15 µm.

In greater detail, the first trench 25 completely laterally surrounds, at a distance, the guard ring 16. Further, the first trench 25 comprises a top portion 26a and a bottom portion 26b.

The top portion 26a of the first trench 25 extends through the first top dielectric region 20, the first heavily doped layer 8, and a part of the first lightly doped layer 6. To a first approximation, locally the top portion 26a of the first trench 25 has in cross-section the shape of a rectangle.

The bottom portion 26b of the first trench 25 extends in the first lightly doped layer 6 and has a width substantially equal to the width of the top portion 26a. To a first approximation, locally the bottom portion 26b of the first trench 25 has in cross-section an elliptical shape. Purely by way of example, the top portion 26a of the first trench 25 has a width comprised, for example, between 1 µm and 2 µm.

The optoelectronic device 1 further comprises a first biasing region 30, as well as a first inner coating region 32 and a second inner coating region 34 and a first outer coating region 36 and a second outer coating region 38, which are arranged inside the first trench 25.

In detail, the first inner coating region 32 is made, for example, of silicon oxide and coats the inner side wall, i.e., the side wall facing the anode region 12, of the top portion 26a of the first trench 25. The first outer coating region 36 is also made of silicon oxide and coats the outer side wall, i.e., the side wall opposite to the inner side wall, of the top portion 26a of the first trench 25. Both the first inner coating region 32 and the first outer coating region 36 have a thickness of, for example, 25 nm.

The second inner coating region 34 is made, for example, of TEOS oxide and coats the first inner coating region 32. The second outer coating region 38 is also made of TEOS oxide and coats the first outer coating region 36. Both the second inner coating region 34 and the second outer coating region 38 have a thickness of, for example, 0.4 µm.

The first biasing region 30 is made, for example, of polysilicon with doping of a P type (doped, for example, with boron) and extends within the first trench 25 following, to a first approximation, the shape thereof. The first biasing region 30 then comprises a respective top portion 31a and a respective bottom portion 31b.

The top portion 31a of the first biasing region 30 extends in the top portion 26a of the first trench 25, between the second inner coating region 34 and the second outer coating region 38, with which it is in direct contact. The top portion 31a of the first biasing region 30 is separate from the first heavily doped layer 8 and from the first lightly doped layer 6, on account of interposition of the first and second inner coating regions 32, 34, as well as of the first and second outer coating regions 36, 38.

The bottom portion 31b of the first biasing region 30 extends in the bottom portion 26b of the first trench 25. To a first approximation, the bottom portion 31b of the first biasing region 30 has in cross-section an elliptical shape.

In addition, the semiconductor body 2 comprises a further semiconductor region 39 of a P+ type, which in what follows will be referred to as the "first buried region 39".

The first buried region 39 surrounds laterally and underneath the bottom portion 26b of the first trench 25, and hence the bottom portion 31b of the first biasing region 30; consequently, the first buried region 39 is arranged between the bottom portion 31b of the first biasing region 30 and the first lightly doped layer 6, with which it is in direct contact. For example, the first buried region 39 has a doping level of $10^{20}$ cm$^{-3}$ and a thickness comprised between 0.1 µm and 0.2 µm.

A portion of the first biasing region 30 further extends over the reference surface $S_{ref}$, in contact with the first top dielectric region 20.

Once again with reference to the first top dielectric region 20, it extends over the top surface $S_{sup}$ for overlying a portion of the first heavily doped layer 8 that surrounds laterally, and in direct contact, the guard ring 16. Further, without any loss of generality, the first top dielectric region 20 overlies a peripheral portion of the guard ring 16, but does not extend over the anode region 12, with respect to which it is laterally staggered. In practice, the first top dielectric region 20 forms an opening 40, over the anode region 12.

The optoelectronic device 1 further comprises a second top dielectric region 42, which is made, for example, of TEOS oxide and has a thickness of, for example, 1.2 µm.

The second top dielectric region 42 extends over the first top dielectric region 20, as well as over the first biasing region 30. For simplicity of representation, in FIG. 1 the second top dielectric region 42 is shown with a respective top surface of a plane type, i.e., not exactly conformal with the underlying structure.

The second top dielectric region 42 concurs in forming the opening 40; in fact, the second top dielectric region 42 does not extend over the anode region 12.

The optoelectronic device 1 further comprises a third top dielectric region 44 and a second biasing region 46.

The second biasing region 46 is made, for example, of polysilicon with a doping of P type, has a thickness of, for example, 50 nm and extends within the opening 40. In particular, the second biasing region 46 extends in contact with the anode region 12 and with an inner portion of the guard ring 16; further, the second biasing region 46 coats the side walls of the opening 40, contacting the first and second top dielectric regions 20, 42. In addition, a peripheral portion of the second biasing region 46 extends over the second top dielectric region 42.

The third top dielectric region 44 is made, for example, of TEOS oxide and has a thickness of, for example, 0.8 µm. Further, the third top dielectric region 44 extends over the second top dielectric region 42, as well as over the second biasing region 46. The third top dielectric region 44 hence extends inside the opening 40.

The optoelectronic device 1 further comprises a first top metallization 50 and a second top metallization 52, each of which is formed, purely by way of example, by a multilayer region including a respective titanium region (not shown), which surrounds an inner region (not shown) made, for example, of an alloy of aluminum, silicon, and copper.

Irrespective of the details of implementation, the first top metallization 50 extends through the third top dielectric region 44, until it contacts with the second biasing region 46. For example, in top plan view, the first top metallization 50 has a ring shape. The first top metallization 50 enables, together with the bottom metallization 18, biasing of the aforementioned PNI junction of the Geiger-mode avalanche photodiode. In addition, the first top metallization 50 makes it possible to collect the aforementioned first output signal of the optoelectronic device 1, generated by the Geiger-mode avalanche photodiode.

The second top metallization 52 extends through the second and third top dielectric regions 42, 44, until it comes into contact with the first biasing region 30. For example, in top plan view, the second top metallization 52 has a ring shape. Further, the second top metallization 52 enables biasing of the PN junction formed by the first buried region 39 and by the first lightly doped layer 6, this junction being to a first approximation of a vertical type.

In use, the PN junction formed by the first buried region 39 and by the first lightly doped layer 6 is reverse biased for depleting the portion of first lightly doped layer 6 surrounded by the first buried region 39, in addition to part of the first buried region 39 itself. In practice, depletion of the first lightly doped layer 6 occurs in a progressive way, as the biasing voltage increases, starting from the interface with the first buried region 39. Further, the depleted region (shown qualitatively in FIG. 1, where it is designated by DZ) does not extend within the first heavily doped layer 8 on account of the high doping of the latter and of the presence of the first and second inner coating regions 32, 34. Likewise, the depleted region DZ does not extend in the substrate 4, on account of the high level of doping of the latter. In addition, the dielectric coating of the side walls of the first trench 25 prevents onset of early breakdown of the junction between the first biasing region 30 and the first heavily doped layer 8, which would prevent proper depletion of the first lightly doped layer 6.

In practice, the PN junction formed by the first buried region 39 and by the first lightly doped layer 6 and the PNI junction of the Geiger-mode avalanche photodiode are decoupled from one another. Further, the first lightly doped layer 6 functions as layer for absorption of infrared radiation.

The first output signal of the optoelectronic device 1 is proportional to the intensity of blue radiation. Instead, at the second top metallization 52 a second output signal is available, which is directly proportional to the intensity of the infrared radiation, so that the embodiment shown in FIG. 1 is a semiconductor device sensitive in the blue and infrared bands.

According to a different embodiment, shown in FIG. 2, the semiconductor body 2 comprises a further pair of epitaxial layers 66, 68, which will be referred to hereinafter, respectively, as the "second lightly doped layer 66" and the "second heavily doped layer 68".

In detail, the second heavily doped layer 68 overlies, in direct contact, the first lightly doped layer 6, is of an N+ type, has a thickness of, for example, 2 μm and has a doping level of, for example, $1 \cdot 10^{18}$ cm$^{-3}$.

The second lightly doped layer 66 overlies, in direct contact, the second heavily doped layer 68, is of an N-- type, has a thickness of, for example, 3 μm and has a doping level of, for example, $1 \cdot 10^{14}$ cm$^{-3}$.

Figure 2:
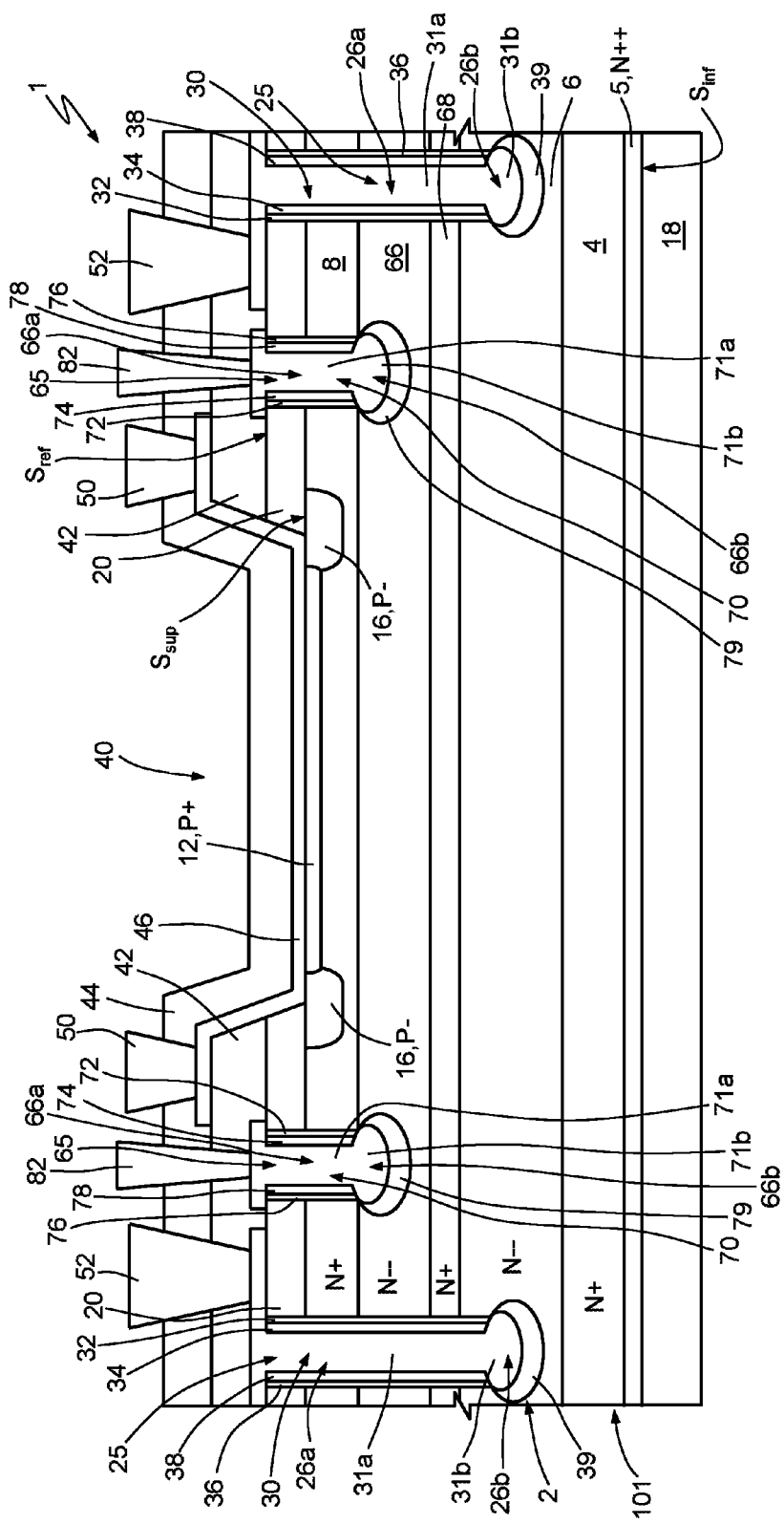

In the embodiment shown in FIG. 2, the first heavily doped layer 8 hence overlies the second lightly doped layer 66. Further, without any loss of generality, the first lightly doped layer 6 and the first heavily doped layer 8 have thicknesses respectively of, for example, 5 μm and 3 μm, whereas the first trench 25 has a depth, for example, comprised between 8 μm and 13 μm (for example, 8.5 μm).

The optoelectronic device 1 further comprises a second trench 65, which in top plan view has, for example, a ring shape, such as (to a first approximation) the shape of an annulus.

In detail, the second trench 65 is surrounded, at a distance, by the first trench 25. Further, the second trench 65 extends through the first top dielectric region 20, starting from the reference surface $S_{ref}$, as well as through the first heavily doped layer 8 and a top portion of the second lightly doped layer 66. For instance, the second trench 65 has a depth comprised between 3 μm and 6 μm (for example, 3.3 μm).

In greater detail, the second trench 65 surrounds the guard ring 16 at a distance. Further, the second trench 65 comprises a top portion 66a and a bottom portion 66b.

The top portion 66a of the second trench 65 extends through the first top dielectric region 20 and the first heavily doped layer 8. To a first approximation, locally the top portion 66a of the second trench 65 has in cross-section the shape of a rectangle.

The bottom portion 66b of the second trench 65 extends in a top portion of the second lightly doped layer 66 and has a width substantially equal to the width of the top portion 66a. To a first approximation, locally the bottom portion 66b of the second trench 65 has in cross-section an elliptical shape. Further, purely by way of example, the top portion 66a of the second trench 65 has a width for example comprised between 1 μm and 2 μm.

Even though in the embodiment shown in FIG. 2 the top portion 66a of the second trench 65 does not extend in the second lightly doped layer 66, embodiments (not shown) are in any case possible of the same type as the one represented in FIG. 2, but where the top portion 66a of the second trench 65 extends in a top portion of the second lightly doped layer 66.

Once again with reference to FIG. 2, the optoelectronic device 1 further comprises a third biasing region 70, as well as a third inner coating region 72 and a fourth inner coating region 74 and a third outer coating region 76 and a fourth outer coating region 78, which are arranged inside the second trench 65.

In detail, the third inner coating region 72 is made, for example, of silicon oxide and coats the inner side wall, i.e., the side wall facing the anode region 12, of the top portion 66a of the second trench 65. The third outer coating region 76 is also made of silicon oxide and coats the outer side wall, i.e., the side wall opposite to the inner side wall, of the top portion 66a of the second trench 65. Both the third inner coating region 72 and the third outer coating region 76 have a thickness, for example, of 25 nm.

The fourth inner coating region 74 is made, for example, of TEOS oxide and coats the third inner coating region 72. The fourth outer coating region 78 is also made of TEOS oxide and coats the third outer coating region 76. Both the fourth inner coating region 74 and the fourth outer coating region 78 have a thickness of, for example, 0.4 μm.

The third biasing region 70 is made, for example, of polysilicon with a doping of a P type and extends within the second trench 65 following, to a first approximation, the shape thereof. The third biasing region 70 then comprises a respective top portion 71a and a respective bottom portion 71b.

The top portion 71a of the third biasing region 70 extends in the top portion 66a of the second trench 65, between the fourth inner coating region 74 and the fourth outer coating region 78, with which it is in direct contact. The top portion 71a of the third biasing region 70 is separate from the first heavily doped layer 8, on account of interposition of the third and fourth inner coating regions 72, 74.

The bottom portion 71b of the third biasing region 70 extends in the bottom portion 66b of the second trench 65. To a first approximation, the bottom portion 71b of the third biasing region 70 has in cross-section an elliptical shape.

In addition, the semiconductor body 2 comprises a further semiconductor region 79 of a P+ type, which in what follows will be referred to as the "second buried region 79".

The second buried region 79 surrounds laterally and underneath the bottom portion 66b of the second trench 65, and hence the bottom portion 71b of the third biasing region 70; consequently, the second buried region 79 is arranged between the bottom portion 71b of the third biasing region 70 and the second lightly doped layer 66, with which it is in direct contact. For example, the second buried region 79 has a doping level of $10^{20}$ cm$^{-3}$ and a thickness comprised between 0.1 μm and 0.2 μm.

A top portion of the third biasing region 70 further extends over the reference surface $S_{ref}$, in contact with the first top dielectric region 20.

The optoelectronic device 1 further comprises a third top metallization 82, which extends through the second and third top dielectric regions 42, 44, until it comes into contact with the third biasing region 70. The third top metallization 82 enables biasing of the PN junction formed by the second buried region 79 and by the second lightly doped layer 66, this junction being to a first approximation of a vertical type.

In use, the PN junction formed by the second buried region 79 and by the second lightly doped layer 66 is reverse biased, for depleting the portion of second lightly doped layer 66 surrounded by the second buried region 79, in addition to part of the second buried region 79 itself. In a way similar to what has been described with reference to depletion of the first lightly doped layer 6, also depletion of the second lightly doped layer 66 occurs in a progressive way, as the biasing voltage increases. Further, the depleted region (not shown) does not extend within the first heavily doped layer 8, thanks to the presence of the third and fourth inner coating regions 72, 74, or inside the second heavily doped layer 68.

In practice, the PN junction formed by the first buried region 39 and by the first lightly doped layer 6, the PN junction formed by the second buried region 79 and by the second lightly doped layer 66 and the PNI junction of the Geiger-mode avalanche photodiode are decoupled from one another, thanks to the presence of the first and second heavily doped layers 8, 68. Further, thanks to the depletion and to the arrangement inside the semiconductor body 2, in the second lightly doped layer 66 there is favored absorption of photons with wavelength in the green band, whereas in the first lightly doped layer 6 absorption of the photons in the red band is favored. It follows that the first and second output signals of the optoelectronic device 1 are proportional, respectively, to the intensity of blue radiation and of red radiation, whereas at the third top metallization 82 a third output signal is available, which is directly proportional to the intensity of green radiation. The embodiment shown in FIG. 2 is hence an RGB sensor. Further, the aforementioned vertical junctions guarantee wide junction areas and a high carrier-collection efficiency, as well as low optical losses caused by undesirable reflections.

Figure 3:
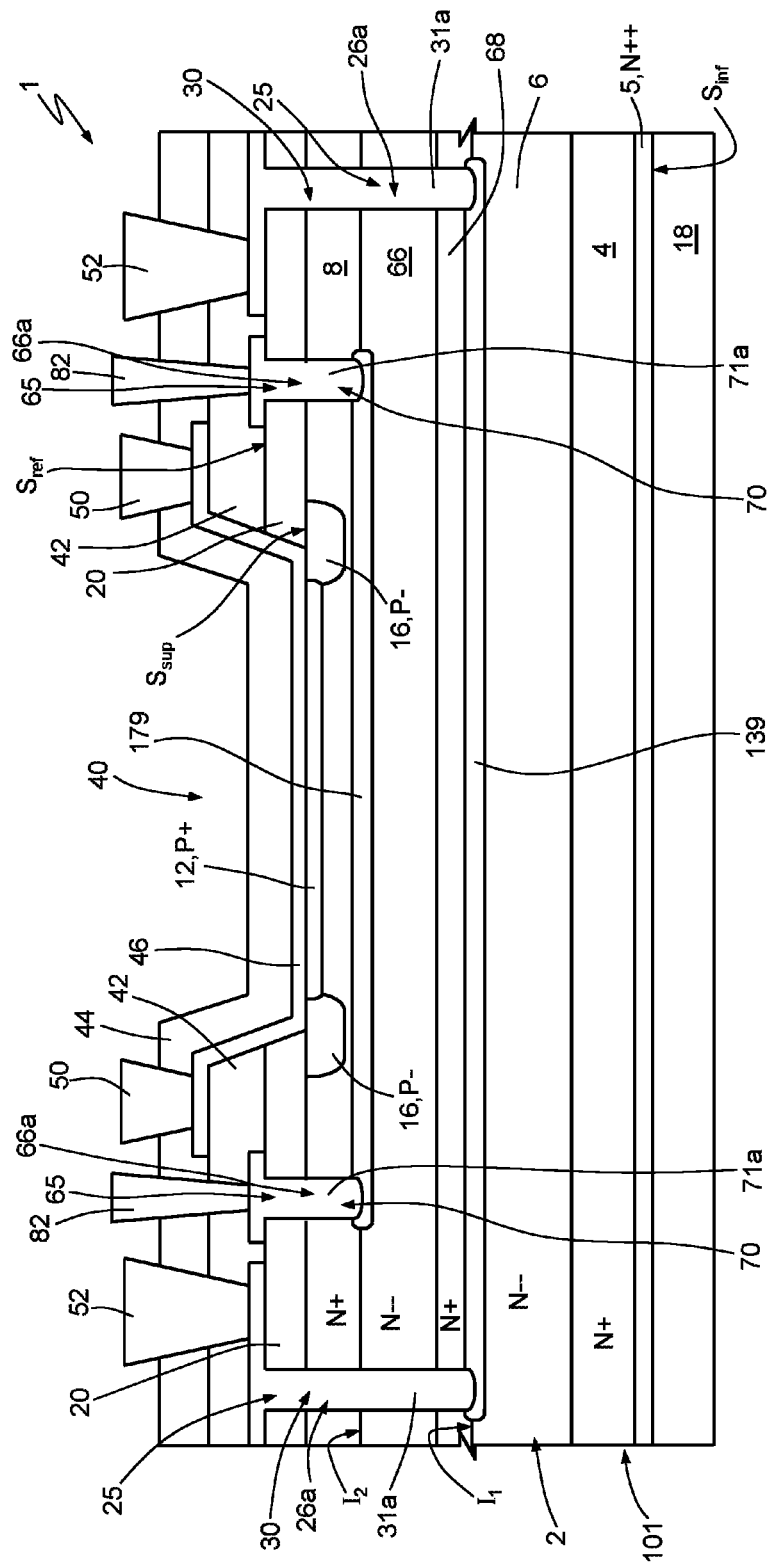

FIG. 3 shows a further embodiment, where the first, second, third, and fourth inner coating layers 32, 34, 72, 74 and the first, second, third, and fourth outer coating layers 36, 38, 76, 78 are absent, so that the top portions 31a and 71a of the first and third biasing regions 30, 70 directly contact the semiconductor body 2.

In addition, in the embodiment shown in FIG. 3, the bottom portion 31b of the first biasing region 30 and the bottom portion 71b of the third biasing region 70 are absent; hence, also the bottom portion 26b of the first trench 25 and the bottom portion 66b of the second trench 65 are absent. Further, the first buried region (here designated by 139) has a substantially planar shape and extends between the first lightly doped layer 6 and the second heavily doped layer 68; more precisely, if $I_1$ is the interface between the first lightly doped layer 6 and the second heavily doped layer 68, the first buried region 139 extends straddling the interface $I_1$, hence it extends in part inside the first lightly doped layer 6 and in part inside the second heavily doped layer 68. The second buried region (here designated by 179) has a substantially planar shape and extends between the second lightly doped layer 66 and the first heavily doped layer 8; more precisely, if $I_2$ is the interface between the second lightly doped layer 66 and the first heavily doped layer 8, the second buried region 179 extends straddling the interface $I_2$, hence it extends in part inside the second lightly doped layer 66 and in part inside the first heavily doped layer 8.

Both the first buried region 139 and the second buried region 179 have a doping level, for example, of $10^{20}$ cm$^{-3}$ and a thickness, for example, comprised between 0.1 µm and 0.2 µm.

The first trench 25 coincides with its own top portion 26a, which surrounds at a distance the second buried region 179 and extends until it traverses a top portion of the first buried region 139. Consequently, in the embodiment shown in FIG. 3, the first trench 25 does not extend within the first lightly doped layer 6. As mentioned previously, the first biasing region 30 coincides with its own first top portion 31a, which fills the first trench 25.

The second trench 65 coincides with its own top portion 66a, which surrounds at a distance the guard ring 16 and extends until it comes into contact with the second buried region 179. In the embodiment shown in FIG. 3, the second trench 65 does not traverse completely the second buried region 179, and hence does not contact the second lightly doped layer 66. As mentioned previously, the third biasing region 70 coincides with its own first top portion 71a, which fills the second trench 65.

In practice, the PN junction formed by the first buried region 139 and by the first lightly doped layer 6 is of a horizontal type; further, also the PN junction formed by the second buried region 139 and by the second lightly doped layer 66 is of a horizontal type. For this reason, the layers that are active for the purposes of depletion, i.e., the first and second lightly doped layers 6, 66 deplete vertically, instead of horizontally; consequently, depletion of these layers may be obtained with very low reverse voltages (in the region of a few volts). Further, the embodiment shown in FIG. 3 does not require the presence of a dielectric coating inside the trenches.

Figure 4:
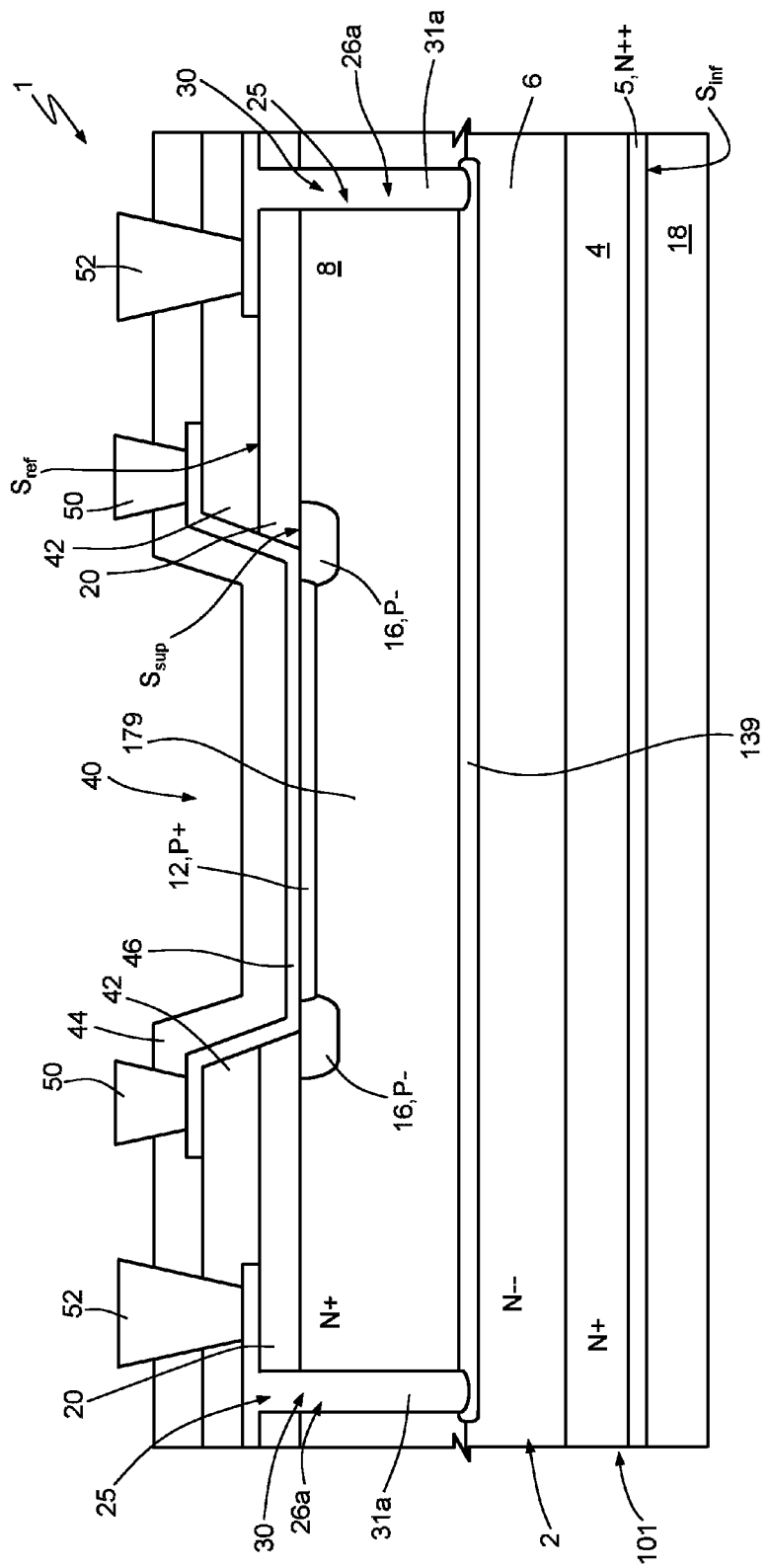

As shown in FIG. 4, further possible are embodiments of the type represented in FIG. 3, but where the second buried region 179, the second trench 65, the third biasing region 70, the second lightly doped layer 66, and the second heavily doped layer 68 are absent.

Figure 5:
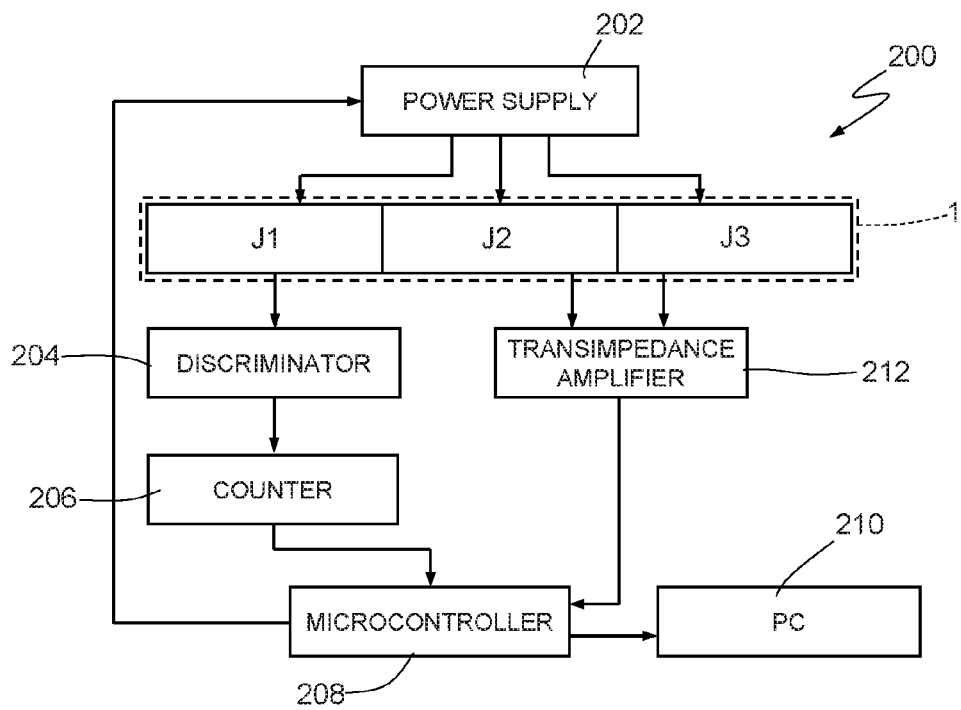
FIG. 5 shows a block diagram of a detection system including the present optoelectronic device.

Purely by way of example, FIG. 5 shows a detection system 200, which includes the optoelectronic device 1, and in particular, by way of example, the embodiment shown in FIG. 2. In FIG. 5, the PNI junction of the Geiger-mode avalanche photodiode is designated by J1, the PN junction formed by the second buried region 79 and by the second lightly doped layer 66 is designated by J2, and the PN junction formed by the first buried region 39 and by the first lightly doped layer 6 is designated by J3. The junctions J1, J2, J3 are electrically accessible, respectively, through the first, third, and second top metallizations 50, 82, 52.

In detail, the detection system 200 comprises a power supply 202, which is configured to (reverse) bias by turns the junctions J1, J2, J3.

The detection system 1 further comprises a discriminator 204 and a counter 206.

The discriminator 204 is electrically connected to the junction J1 for receiving the first output signal of the optoelectronic device 1. Further, if by "event" we indicate exceeding of a current threshold by the first output signal of the optoelectronic device 1, the discriminator 204 generates a signal indicating the events; i.e., it selects just the avalanche currents that have exceeded the aforementioned current threshold; in other words, the discriminator 204 generates a signal that indicates each overstepping of the threshold current by the first output signal. For example, the signal generated by the discriminator 204 may include a pulse, whenever the first output signal exceeds the threshold current.

The counter 206 receives the signal generated by the discriminator 204 and in turn generates a signal indicating the count of the events. Albeit not shown, it is further possible for there to be present a charge integrator, instead of the counter 206.

The signal generated by the counter 204 is supplied to a microcontroller unit 208, which controls power supply 202 for biasing in sequence, and one at a time, the junctions J1, J2, J3. Further, the microcontroller unit 208 determines, on the basis of the signal generated by the counter 206, a corresponding first electrical quantity, indicating the intensity of the luminous flux in the blue. In addition, the microcontroller unit 208 may communicate the first electrical quantity to a computer 210, which enables corresponding display thereof.

The detection system 200 further comprises a transimpedance amplifier 212, which is electrically connected to the junctions J2 and J3, for receiving, by turns, the second and third output signals and generate accordingly an amplified signal, which alternatively indicate the luminous flux in the green and in the red.

Also the amplified signal is supplied to the microcontroller unit 208, which, at alternating time intervals, determines, on the basis of the amplified signal, a second electrical quantity and a third electrical quantity, which indicate, respectively, the intensity of the luminous flux in the green and in the red. The microcontroller unit 208 may communicate also the second and third electrical quantities to the computer 210.

Figure 6:
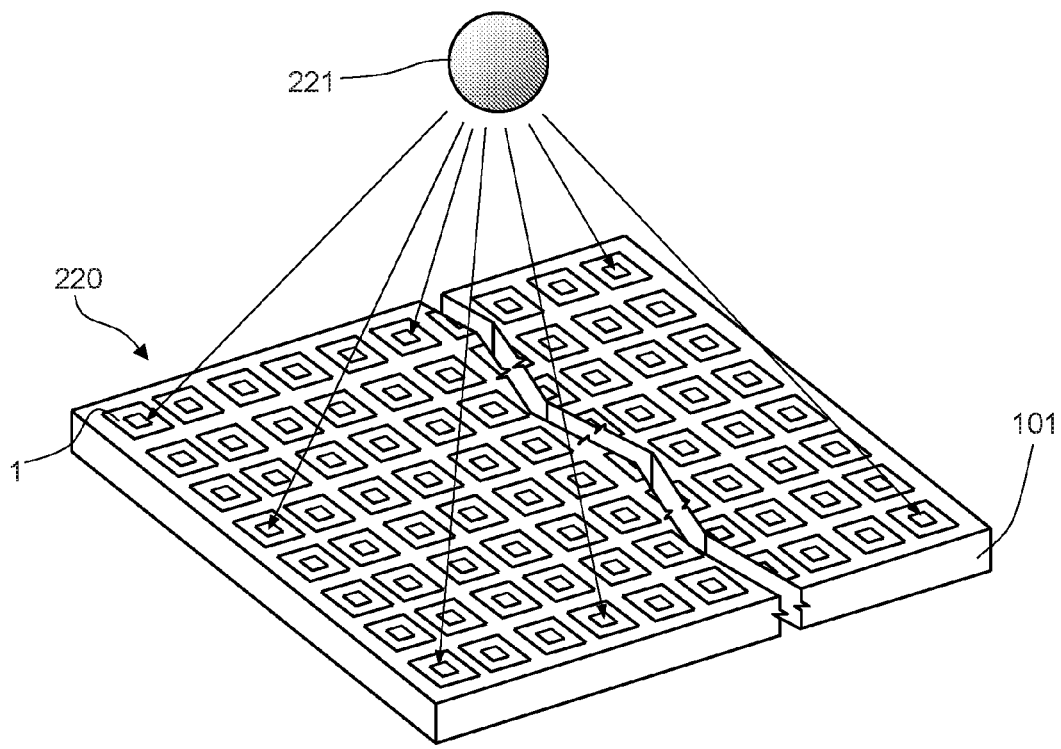
FIG. 6 is a schematic perspective view of a chip including a plurality of optoelectronic devices.

As shown in FIG. 6, the present optoelectronic device 1 may also form part of an array 220, which includes a plurality of optoelectronic devices and is formed in the die 101. In FIG. 6 the array 220 is lit up by a light source 221.

Purely by way of example, the embodiment shown in FIG. 1 may be formed following the manufacturing process described in what follows.

Figure 7:
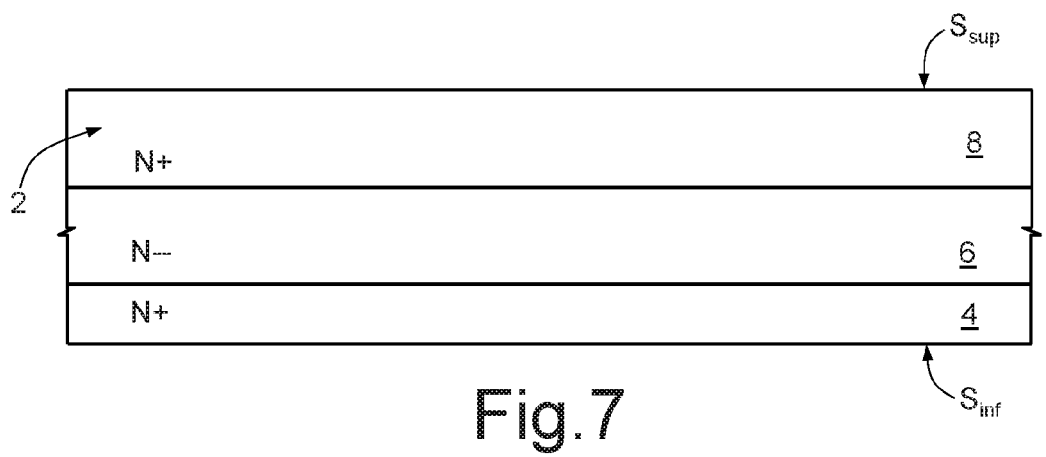
FIGS. 7-28 are schematic cross-sectional views of an embodiment of an optoelectronic device, during successive steps of a manufacturing process.

As shown in FIG. 7, initially the semiconductor body 2 is provided, which includes the substrate 4, the first lightly doped layer 6, and the first heavily doped layer 8. In this step, the bottom surface $S_{inf}$ is formed by the substrate 4.

Figure 8:
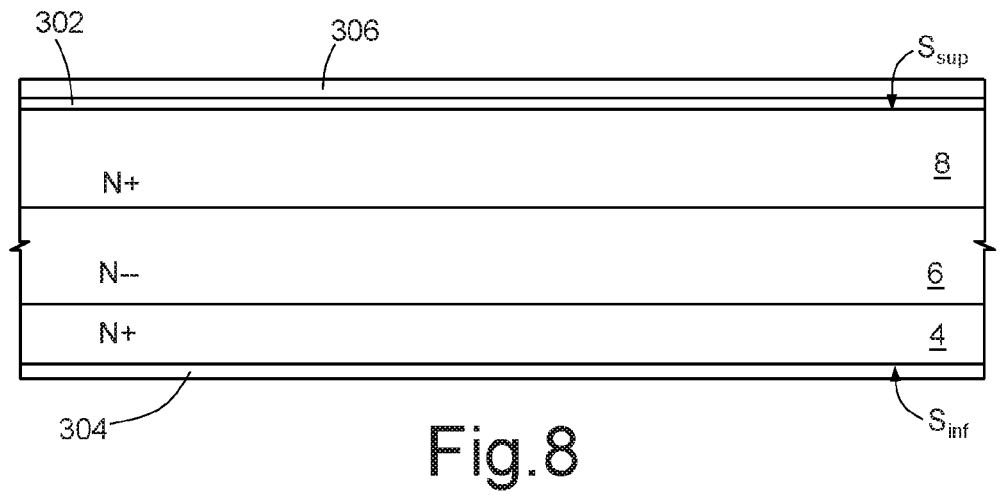

Next, as shown in FIG. 8, a process of thermal oxidation is carried out, which leads to formation of a first thermal-oxide layer 302 and a second thermal-oxide layer 304, which coat, respectively, the top surface $S_{sup}$ and the bottom surface $S_{inf}$ and have a thickness of, for example, 25 nm. Next, formed by deposition on the first thermal-oxide layer 302 is a first TEOS-oxide layer 306, which has a thickness of, for example, 0.8 µm.

Figure 9:
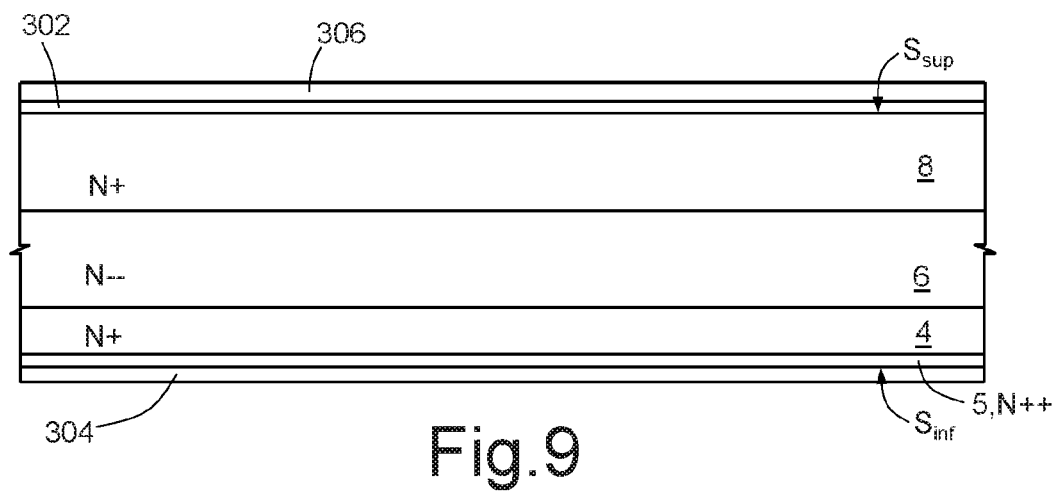

Next, as shown in FIG. 9, a process of implantation of impurities of an N type (for example, phosphorus or arsenic) is carried out on the back of the optoelectronic device 1 for forming the bottom enriched region 5. For example, the implantation process may be carried out with a dose of $5 \cdot 10^{15}$ m$^{-2}$ and an energy of 80 keV. The second thermal-oxide layer 304 functions as pre-implantation oxide.

Figure 10:
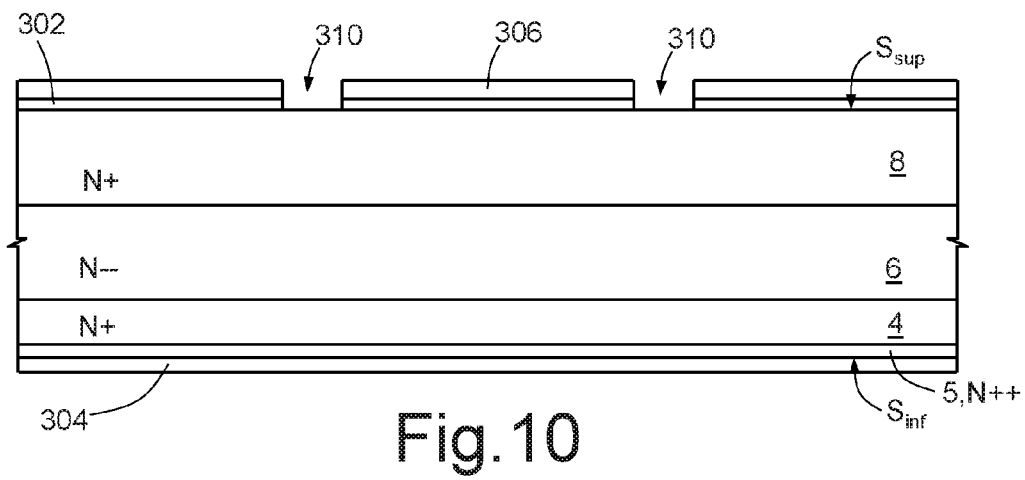

Next, as shown in FIG. 10, by a photolithographic process and a subsequent dry etch a portion of the first TEOS-oxide layer 306 is selectively removed, as well as an underlying portion of the first thermal-oxide layer 302, for forming a first window 310, which has a ring shape, and expose a first portion of the top surface $S_{sup}$.

Figure 11:
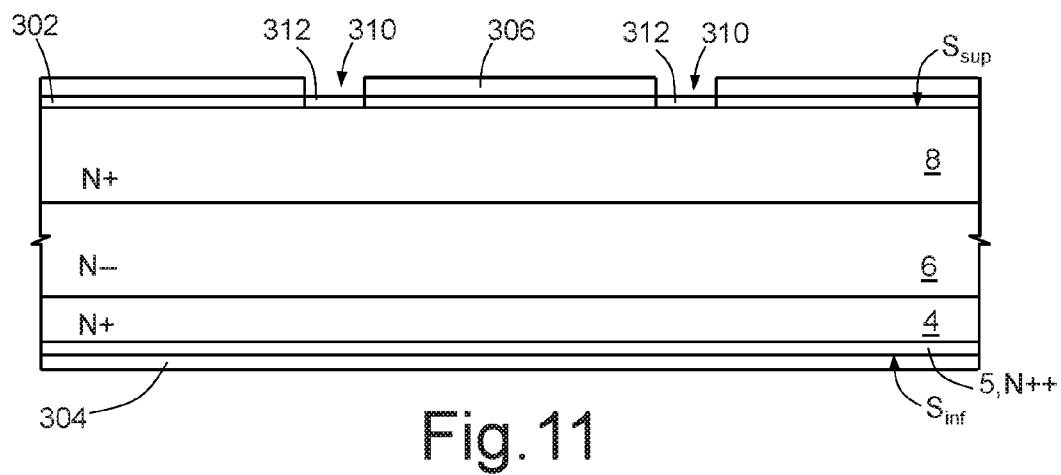

Then, as shown in FIG. 11, a further thermal process is carried out to form, over the exposed portion of top surface $S_{sup}$, a pre-implantation oxide layer 312, of silicon oxide and having a thickness of, for example, 25 nm.

Figure 12:
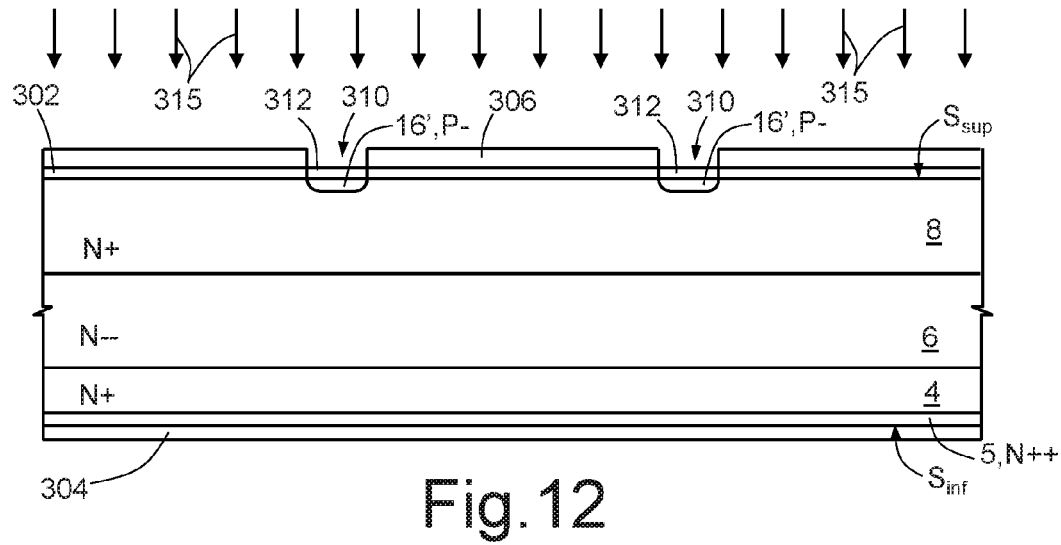

Next, as shown in FIG. 12, a process of implantation of dopant species of a P type (for example, boron ions), represented by the arrows 315, is carried out for locating the dopant species in a first thin layer 16', which gives out onto the top surface $S_{sup}$ and extends in a top portion of the first heavily doped layer 8. The implantation is carried out, for example, with a dose of $5 \cdot 10^{14}$ m$^{-2}$ and an energy of 80 keV.

Figure 13:
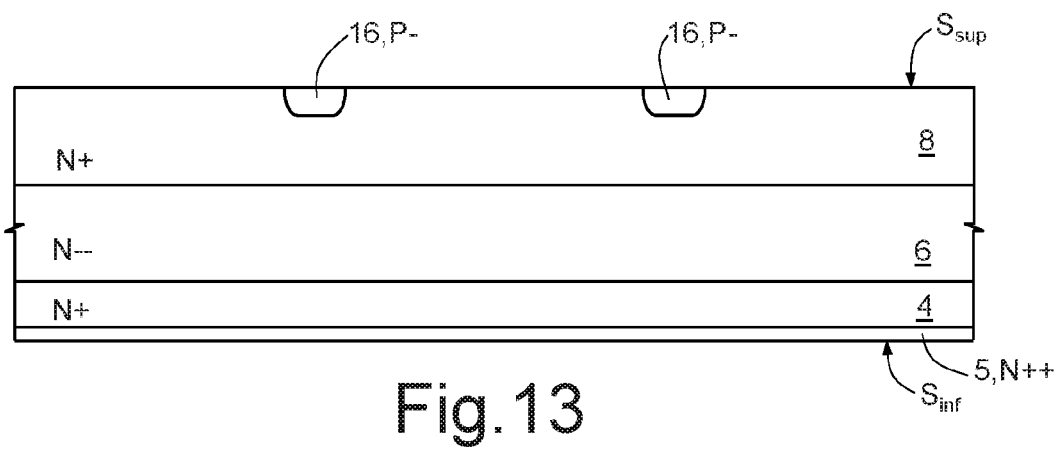

Next, as shown in FIG. 13, a thermal treatment is carried out, following upon which the first thin layer 16' forms the guard ring 16. For example, said thermal treatment occurs in nitrogen environment, at the temperature of 1150° C. and with a duration of three hours. Following upon the thermal treatment, the second thermal-oxide layer 304 and the remaining portions of the first thermal-oxide layer 302 and of the first TEOS-oxide layer 306 are removed by a wet etch.

Figure 14:
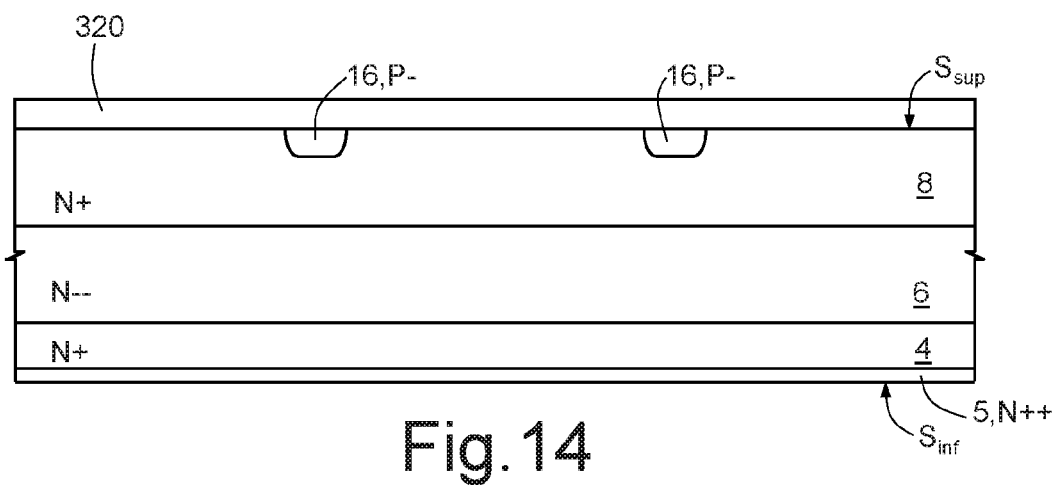

Next, as shown in FIG. 14, formed on the top surface $S_{sup}$ is a second TEOS-oxide layer 320, which has a thickness of, for example, 1.6 µm.

Figure 15:
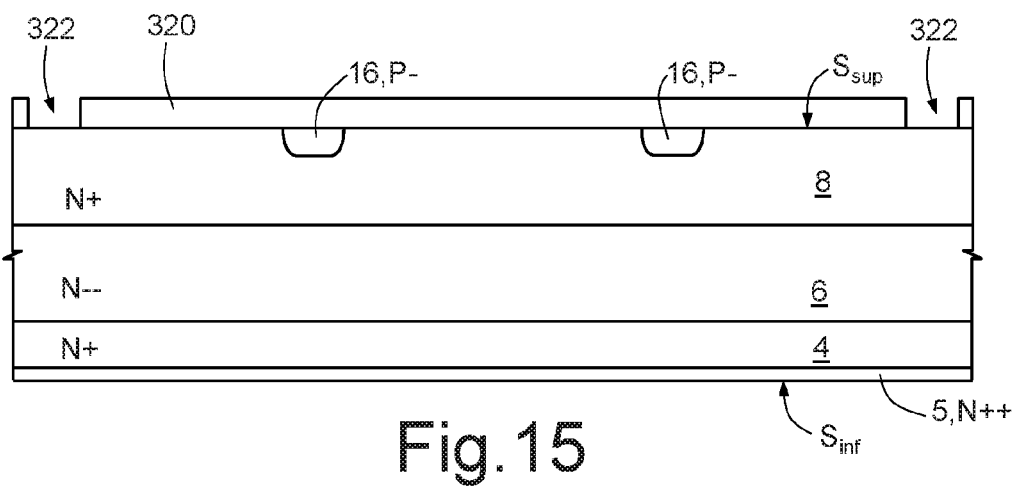

Then, as shown in FIG. 15, by a photolithographic process and a subsequent dry etch a portion of the second TEOS-oxide layer 320 is selectively removed for forming a second window 322 and expose a second portion of the top surface $S_{sup}$.

Figure 16:
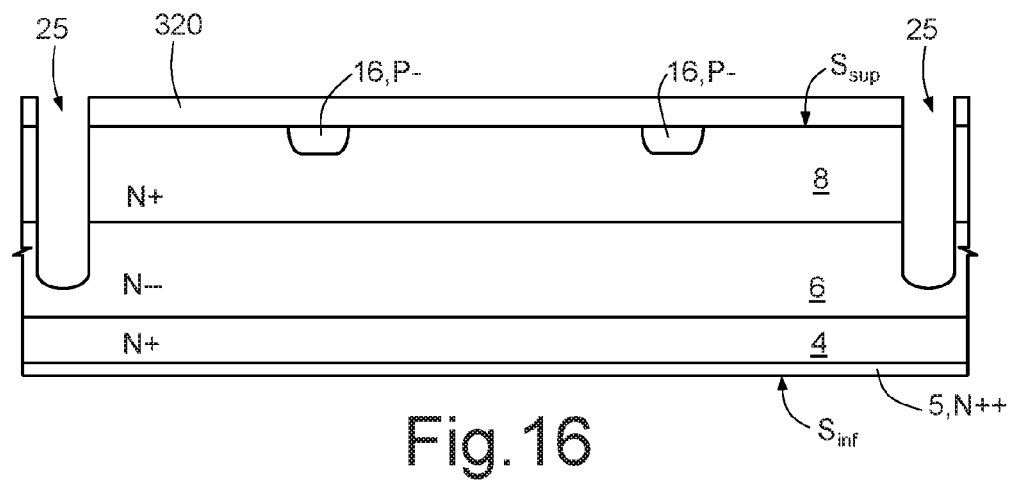

Next, as shown in FIG. 16, the first trench 25 is formed, by carrying out a dry etch, in which the portion of second TEOS-oxide layer 320 that has remained following upon the operations shown in FIG. 15 functions as so-called hard mask. In this step, the first trench 25 has a depth of, for example, 15 µm (i.e., substantially equal to the depth that the first trench 25 will have at the end of the process) and has a width that to a first approximation is uniform.

Figure 17:
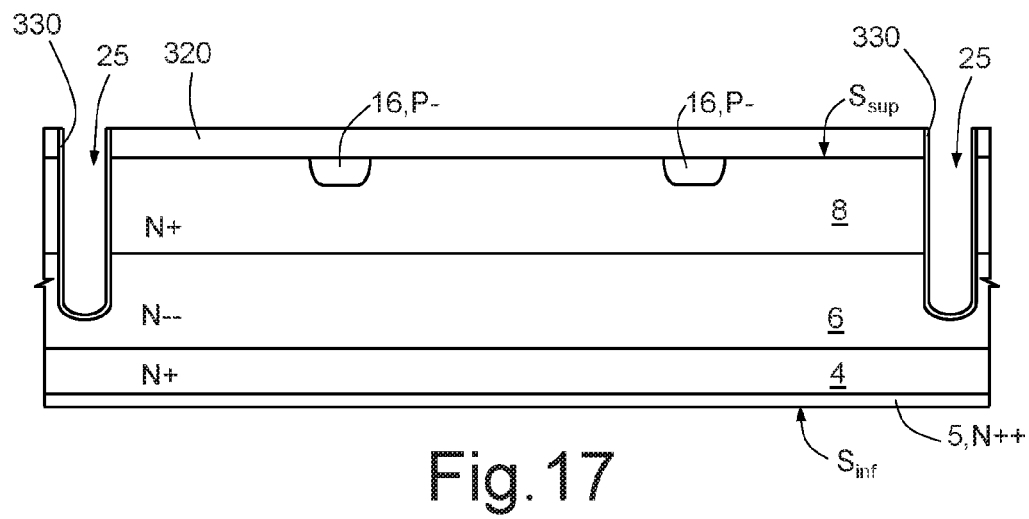

Then, as shown in FIG. 17, a process of thermal oxidation is carried out so that the side walls and the bottom of the first trench 25 are coated with a third thermal-oxide layer 330, which has, for example, a thickness of 25 nm.

Figure 18:
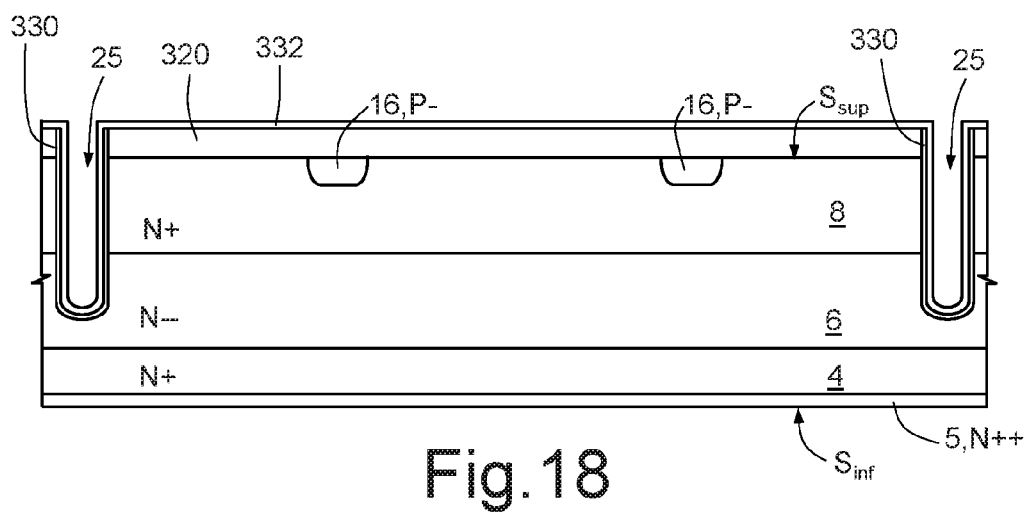

Next, as shown in FIG. 18, deposited on the second TEOS-oxide layer 320 and inside the first trench 25 is a third TEOS-oxide layer 332, which has a thickness of, for example, 0.4 µm. The third TEOS-oxide layer 332 hence coats the third thermal-oxide layer 330 and does not occlude the first trench 25 completely.

Figure 19:
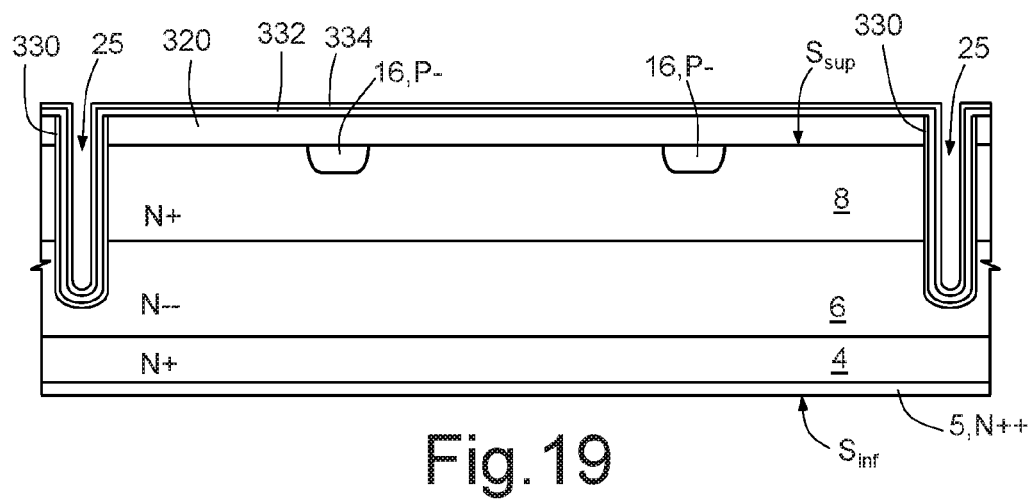

Next, as shown in FIG. 19, formed on the third TEOS-oxide layer 332 is a sacrificial layer 334, made, for example, of silicon nitride Si$_3$N$_4$ or of polymeric material and having a thickness of, for example, 0.8 µm. Inside the first trench 25, the sacrificial layer 334 coats the third TEOS-oxide layer 332, without occluding the first trench 25 completely.

Figure 20:
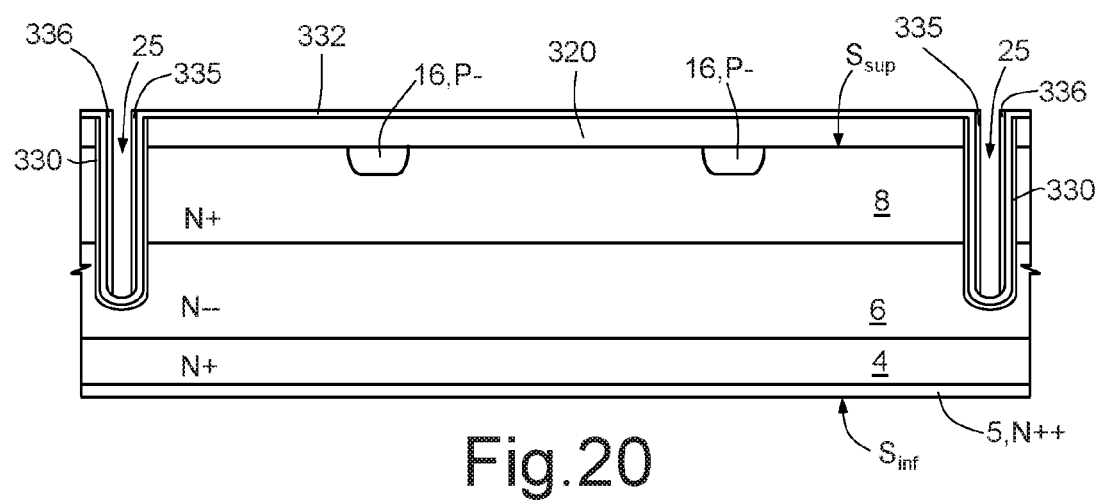

Next, as shown in FIG. 20, by a photolithographic process and a subsequent anisotropic dry etch, a portion of the sacrificial layer 334 that coats the bottom of the first trench 25 and portions of the sacrificial layer 334 located on the outside of the first trench 25 are selectively removed. The remaining portions of sacrificial layer 334 form, respectively, an inner protective layer 335, which coats, at a distance, the inner side wall of the first trench 25, and an outer protective layer 336, which coats, at a distance, the outer side wall of the first trench 25.

Figure 21:
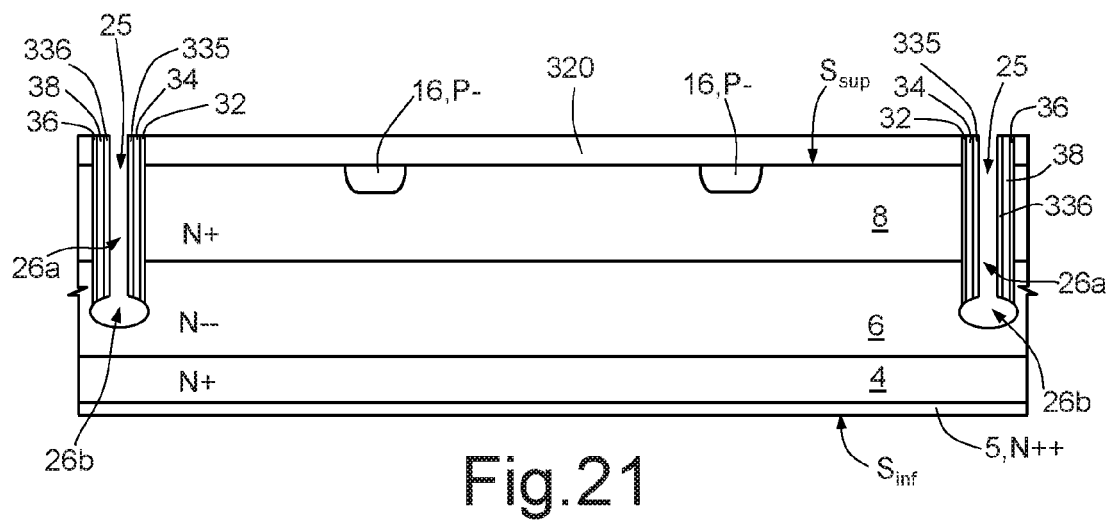

Next, as shown in FIG. 21, a wet etch is carried out for removing selectively portions of the third TEOS-oxide layer 332 and of the third thermal-oxide layer 330 located on the bottom of the first trench 25, as well as the part of third TEOS-oxide layer 332 arranged on the outside of the first trench 25. This wet etch presents a high selectivity in regard to the "hard mask" formed by the inner protective layer 335 and by the outer protective layer 336. Following upon these operations, the first trench 25 includes the respective top portion 26a and the respective bottom portion 26b. Further, the remaining portions of the third thermal-oxide layer 330 form the first inner coating region 32 and the first outer coating region 36, whereas the remaining portions of the third TEOS-oxide layer 332 form the second inner coating region 34 and the second outer coating region 38.

Figure 22:
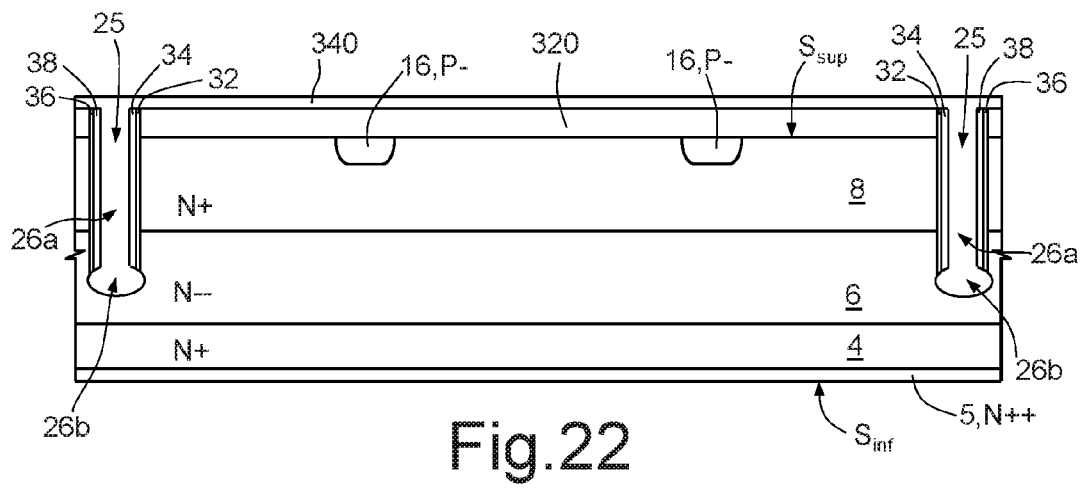

Next, as shown in FIG. 22, the first and second protective layers 335, 336 are removed by a wet etch. Further, a first conductive layer 340, of polysilicon of a P type, is formed by deposition over the second TEOS-oxide layer 320 and inside the first trench 25, for filling the latter. For example, the first conductive layer 340 has a level of doping equal to $10^{20}$ cm$^{-3}$ and has a thickness of 1.2 µm. In greater detail, the first conductive layer 340 contacts, at the bottom of the first trench 25, the first lightly doped layer 6.

Figure 23:
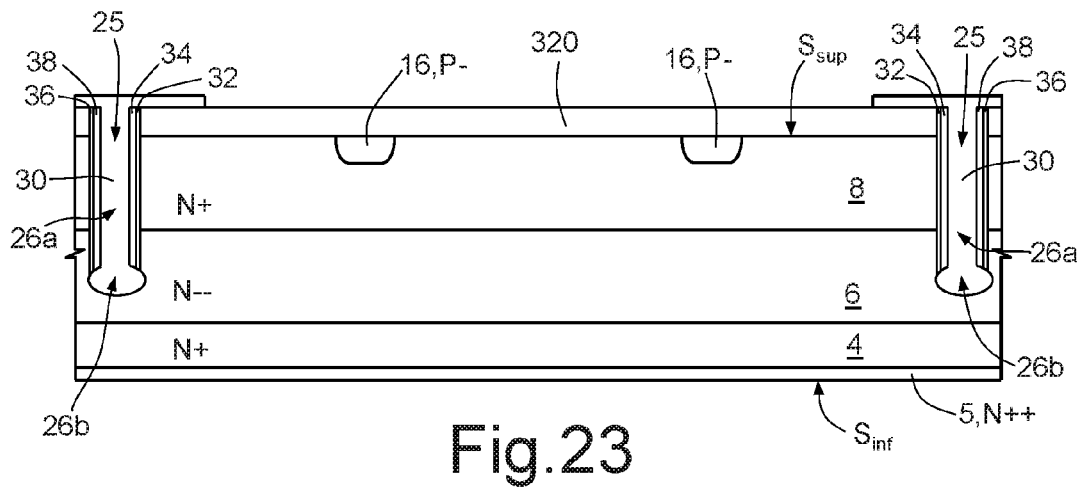

Next, as shown in FIG. 23, a photolithographic process and a subsequent dry etch are carried out for selectively removing portions of the first conductive layer 340. The remaining portion of first conductive layer 340 forms the first biasing region 30.

Figure 24:
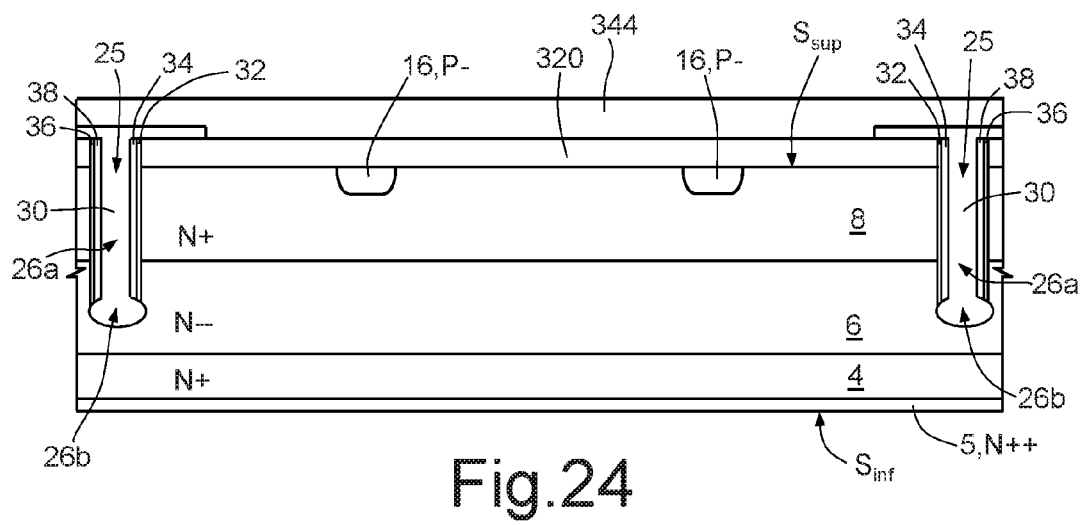

Next, as shown in FIG. 24, deposited over the second TEOS-oxide layer 320 and over the first biasing region 30 is a fourth TEOS-oxide layer, which has a thickness of, for example, 1.2 μm. For simplicity of representation, in FIG. 24 the fourth TEOS-oxide layer 344 is shown with a respective top surface of a plane type, i.e., not exactly conformal with the underlying structure.

Figure 25:
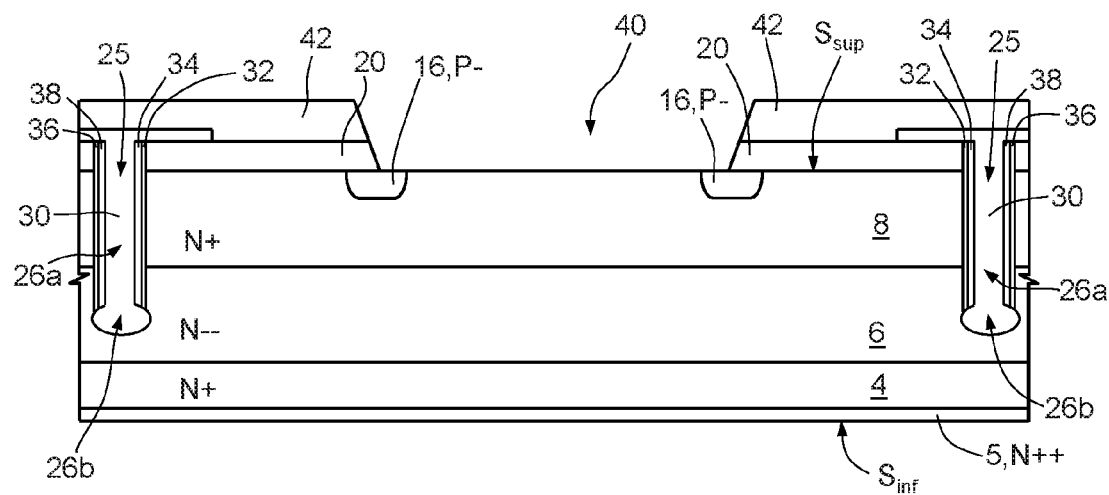

Next, as shown in FIG. 25, a new photolithographic process and a subsequent wet etch are carried out in order to remove a portion of the fourth TEOS-oxide layer 344 and an underlying portion of the second TEOS-oxide layer 320 for forming the opening 40, and thus defining the active area of the optoelectronic device 1. The remaining portions of the second and fourth TEOS-oxide layers 320, 344 form, respectively, the first and second top dielectric regions 20, 42.

Figure 26:
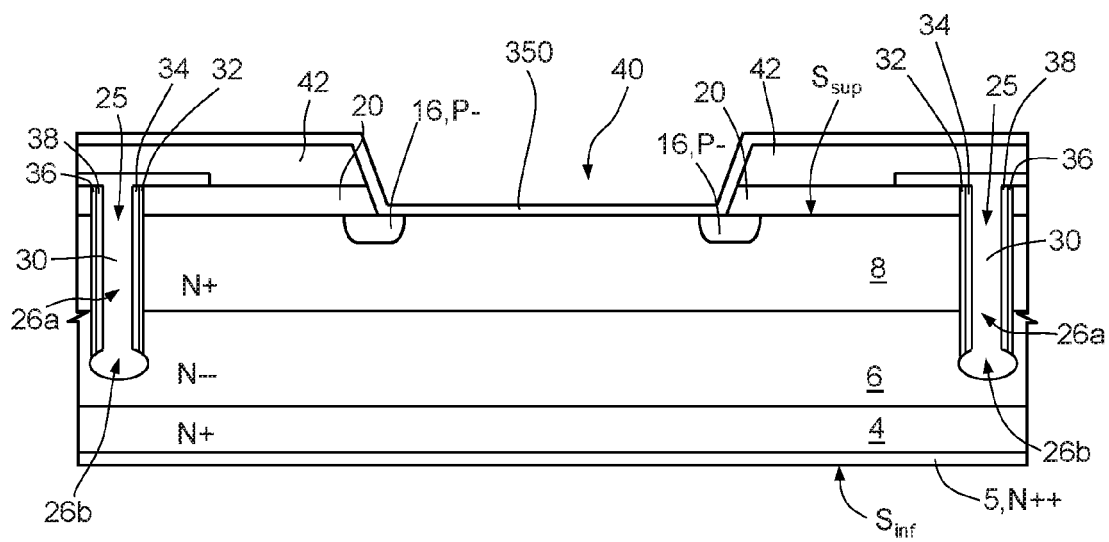

Next, as shown in FIG. 26, a second conductive layer 350 is formed over the second top dielectric region 42 for coating the bottom and the side walls of the opening 40. The second conductive layer 350 is made of polysilicon of a P type, has a doping level of for example $10^{20}$ cm$^{-3}$ and has a thickness of, for example, 50 nm. Further, the second conductive layer 350 contacts the guard ring 16 and the portion of first heavily doped layer 8 enclosed by the guard ring 16.

Figure 27:
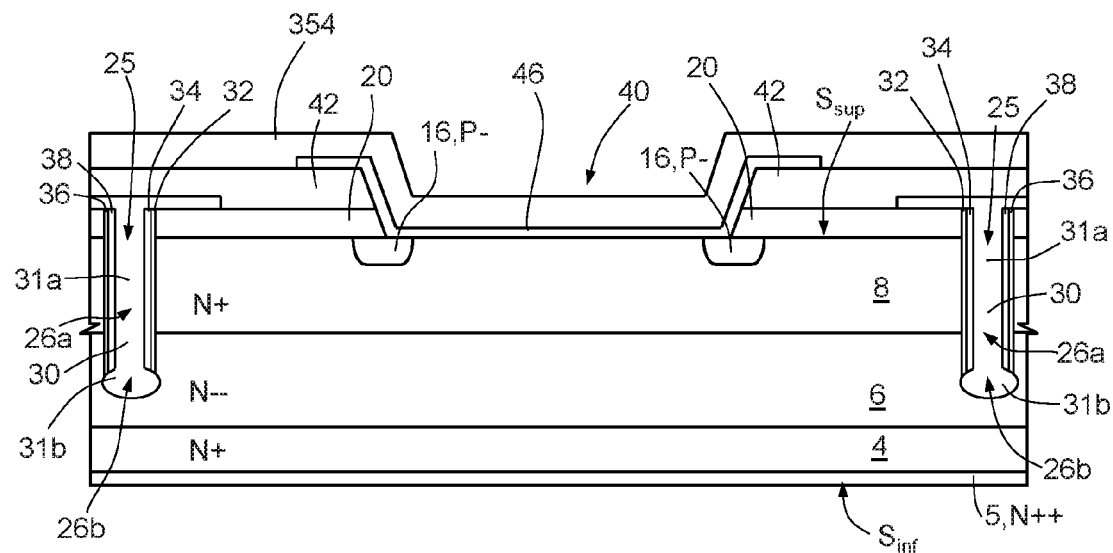

Then, as shown in FIG. 27, a further photolithographic process and a subsequent wet etch are carried out in order to remove selectively a portion of the second conductive layer 350. The remaining portion of the second conductive layer 350 forms the second biasing region 46. Further, as shown once again in FIG. 27, deposited on the second biasing region 46 and on the second top dielectric region 42 is a fifth TEOS-oxide layer 354, which has a thickness of, for example, 0.8 μm.

Figure 28:
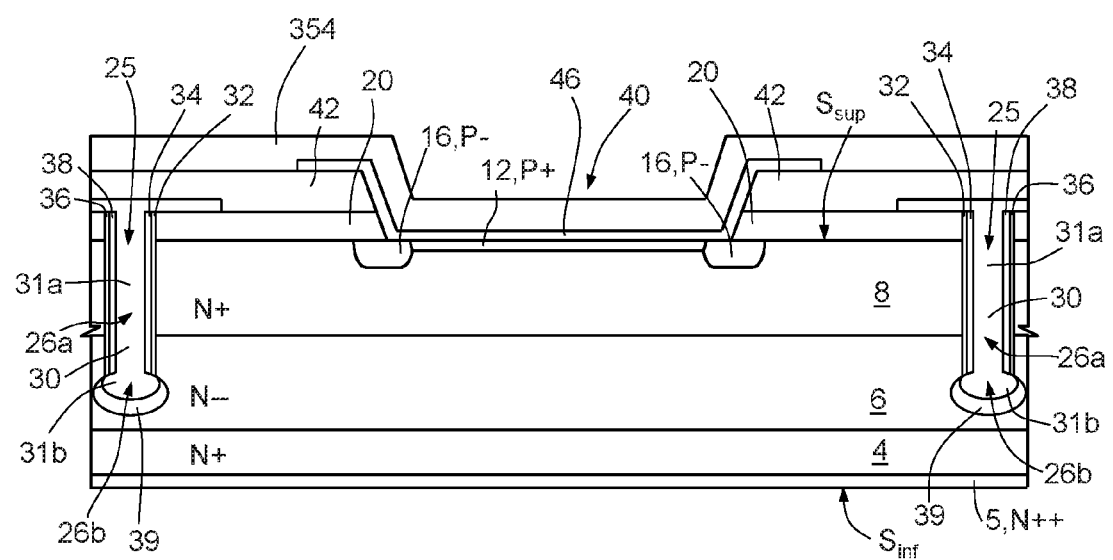

Next, as shown in FIG. 28, a thermal treatment is carried out having the duration of one minute, in nitrogen environment and at the temperature of 1000° C. In this way, the dopant impurities present in the first and second biasing regions 30, 46 diffuse in the semiconductor material that is in direct contact with them.

In particular, the impurities present in the second biasing region 46 diffuse in the portion of the first heavily doped layer 8 enclosed by the guard ring 16, where they form the anode region 12. The impurities present in the bottom portion 31b of the first biasing region 30 diffuse in a portion of the first lightly doped layer 6 that surrounds this bottom portion 31 and form the first buried region 39.

In a per se known manner and consequently not shown, the first and second top metallizations 50, 52 are then formed, as well as the bottom metallization 18.

As regards the embodiment shown in FIG. 2, it may be obtained in a way similar to the embodiment represented in FIG. 1, by digging two trenches at different depths (in the case in point, the first and second trenches 25, 65). For this purpose, the second trench may be dug after the first trench 25 has been dug, hence after the operations shown with reference to FIG. 16 have been carried out, and before carrying out the operations shown with reference to FIG. 17.

As regards the embodiment represented in FIG. 3, it may be obtained by carrying out the operations described in what follows.

Figure 29:
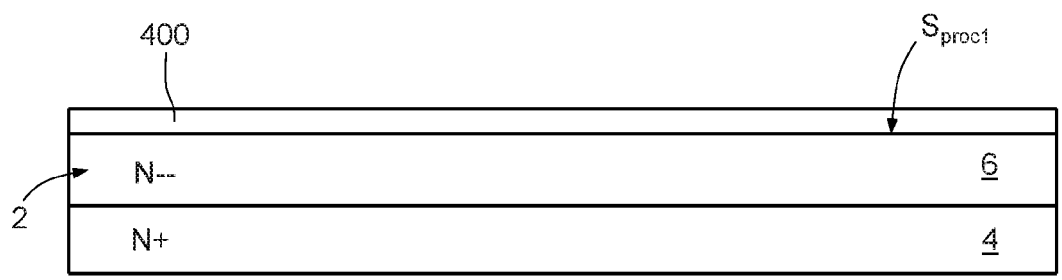
FIGS. 29-33 are schematic cross-sectional views of an embodiment of an optoelectronic device, during successive steps of a manufacturing process.

In detail, as shown in FIG. 29, the semiconductor body 2 is provided, which includes the substrate 4 and the first lightly doped layer 6, which is delimited at the top by a first intermediate surface $S_{proc1}$. Further, deposited on the first intermediate surface $S_{proc1}$ is a sixth TEOS-oxide layer 400, which has a thickness of, for example, 1.6 μm.

Figure 30:
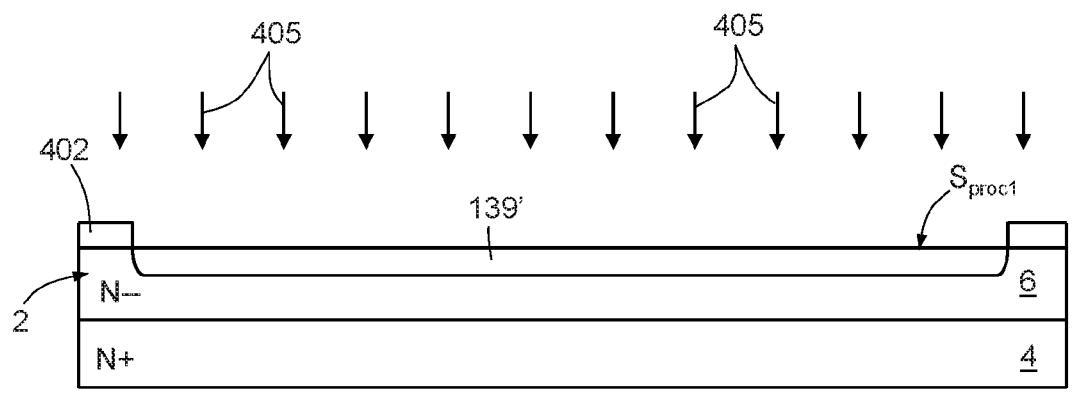

Next, as shown in FIG. 30, a dry etch is carried out for removing selectively a portion of the sixth TEOS-oxide layer 400, exposing a portion of the first intermediate surface $S_{proc1}$. The remaining portion of the sixth TEOS-oxide layer 400 forms a first mask 402. Next, a process of implantation of dopant species of a P type (for example, boron ions), represented by the arrows 405, is carried out for locating the dopant species in a second thin layer 139', which gives out onto the first intermediate surface $S_{proc1}$ and extends in a top portion of the first lightly doped layer 6. The implantation is carried out, for example, with a dose of $5 \cdot 10^{14}$ cm$^{-2}$ and with an energy of 20 keV.

Figure 31:
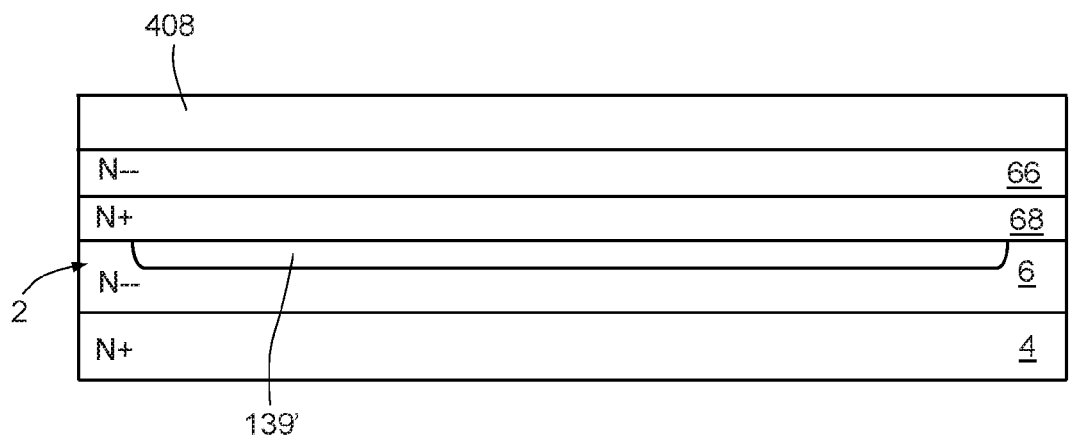

Then, as shown in FIG. 31, the first mask 402 is removed by a wet etch. Further, by epitaxial growth the second heavily doped layer 68 and the second lightly doped layer 66 are formed, laid over which is a seventh TEOS-oxide layer 408, which has a thickness of, for example, 1.6 μm.

Figure 32:
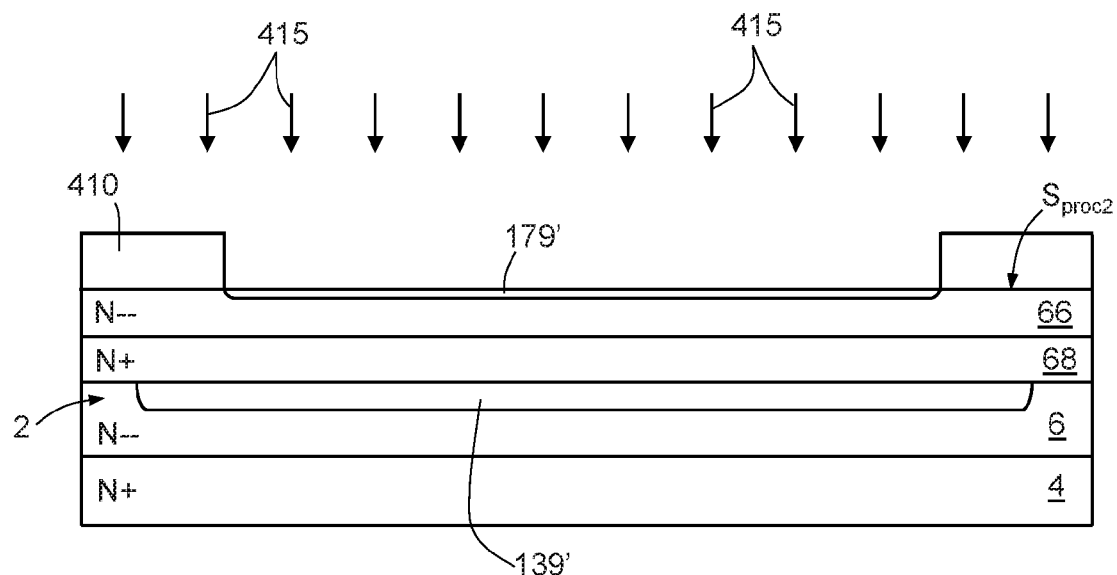

Next, as shown in FIG. 32, a dry etch is carried out for removing selectively a portion of the seventh TEOS-oxide layer 408, exposing a portion of the top surface of the second lightly doped layer 66, which in what follows will be referred to as the "second intermediate surface $S_{proc2}$". The remaining portion of the seventh TEOS-oxide layer 408 forms a second mask 410. Then, a process of implantation of dopant species of a P type (for example, boron ions), represented by the arrows 415, is carried out for locating the dopant species in a third thin layer 179', which gives out onto the second intermediate surface $S_{proc2}$ and extends in a top portion of the second lightly doped layer 66. Implantation is carried out, for example, with a dose of $5 \cdot 10^{14}$ cm$^{-2}$ and an energy of 20 keV.

Figure 33:
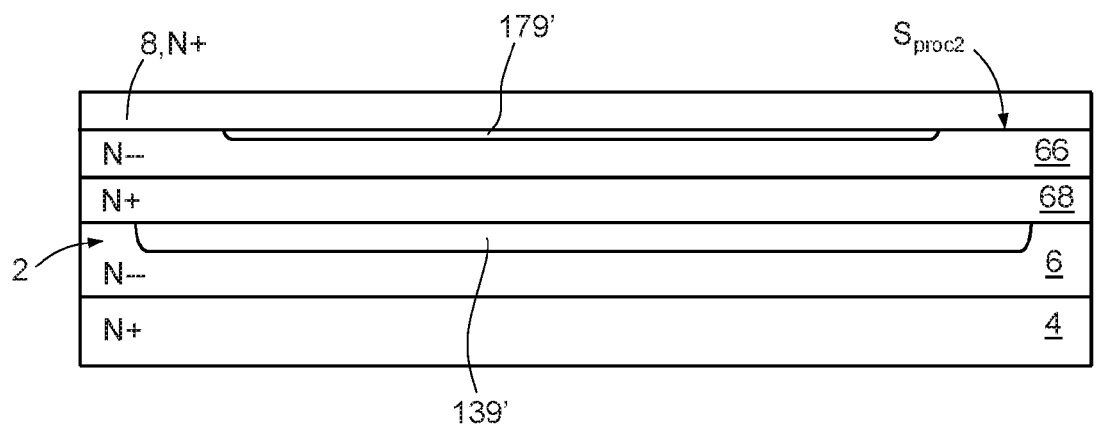

Next, as shown in FIG. 33, the second mask 410 is removed by a wet etch. Then, formed by epitaxial growth on the second intermediate surface $S_{proc2}$ is the first heavily doped layer 8.

Then, the manufacturing process continues as described previously, with reference to FIG. 7 and to the subsequent figures, except for the differences regarding the structure of the semiconductor body 2, as well as the fact that the third thermal-oxide layer 330 and the third TEOS-oxide layer 332 are not formed. Further, the implantation that leads to formation of the first thin layer 16' is carried out with a dose of $5 \cdot 10^{13}$ cm$^{-2}$ and an energy of 50 keV; the subsequent thermal treatment is carried out at a temperature of 1000° C. and with a duration of three hours and entails formation of the first and second buried regions 139, 179, starting from the second and third thin layers 139', 179', respectively.

The advantages that the present optoelectronic device affords emerge clearly from the foregoing discussion. In particular, the present optoelectronic device forms a multiband sensor capable of generating currents, which are proportional to the intensity of the luminous fluxes in corresponding bands; this multiband sensor does not require the use of optical filters. Further, the currents are generated in a way substantially independent of one another, since the depleted regions that are generated, in use, in the optoelectronic device 1 are separated from one another by heavily doped layers, which are electrically inactive and function as buffer layers. This configuration may further be designed for shifting the detection peaks as desired, inside the corresponding bands.

Finally, it is evident that modifications and variations may be made to the present optoelectronic device and to the manufacturing process described, without thereby departing from the scope of the present disclosure.

For example, the types of conductivity of the semiconductor body 2 may be reversed with respect to what has been described.

The semiconductor body 2 may comprise further layers additional to the ones described. For example, embodiments are possible corresponding to embodiments described previously, but where the semiconductor body comprises a further epitaxial layer, which forms the top surface $S_{sup}$, and inside which the anode region 12 extends. Further possible are embodiments where, between the second lightly doped layer 66 and the second heavily doped layer 68, at least one further layer is present having a doping level comprised between the doping levels of the above two layers.

As mentioned previously, the first and third inner coating regions 32, 72 and the first and third outer coating regions 36, 76 may be absent.

Finally, as regards the modalities of use of the present optoelectronic device 1, the junction of the Geiger-mode avalanche photodiode may also be biased for operating in linear regime.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An optoelectronic device for detecting radiation, comprising:
   a semiconductor body including:
      a cathode region delimited by a front surface of the semiconductor body and having a first conductivity type, said cathode region having a lower layer;
      an anode region having a second conductivity type, which extends in the cathode region starting from the front surface and forms a shallow junction with said cathode region; and
      a first buried region having the second conductivity type, which extends within the cathode region and forms a first buried junction with said lower layer; wherein said cathode region further comprises a first buffer layer, which is arranged underneath the anode region and overlies, in direct contact, the lower layer, said first buffer layer having a doping level higher than a doping level of the lower layer;
   a first trench, which traverses the front surface and extends in the cathode region, said first trench including a top portion, which traverses the first buffer layer, and a bottom portion, which extends within the lower layer;
   a first dielectric coating region, which coats side walls of the top portion of the first trench; and
   a first conductive region including a top portion, which extends within the top portion of the first trench, and is surrounded by the first dielectric coating region, and a respective bottom portion, which extends within the bottom portion of the first trench; wherein the first buried region surrounds laterally and underneath the bottom portion of the first conductive region, and directly contacts the bottom portion of the first conductive region.

2. The optoelectronic device according to claim 1, wherein said shallow junction forms a Geiger-mode avalanche photodiode.

3. The optoelectronic device according to claim 1, wherein said shallow junction is configured to generate, in response to radiation that impinges on the front surface, a first current proportional to a light intensity of a first spectral component of said radiation; and wherein said first buried junction is configured to generate a second current proportional to a light intensity of a second spectral component of said radiation.

4. An optoelectronic device for detecting radiation, comprising a semiconductor body including:
   a cathode region delimited by a front surface of the semiconductor body and having a first conductivity type, said cathode region having a lower layer;
   an anode region having a second conductivity type, which extends in the cathode region starting from the front surface and forms a shallow junction with said cathode region;
   a first buried region having the second conductivity type, which extends within the cathode region and forms a first buried junction with said lower layer; wherein said cathode region further comprises a first buffer layer, which is arranged underneath the anode region and overlies, in direct contact, the lower layer, said first buffer layer having a doping level higher than a doping level of the lower layer; and
   a second buried region having the second conductivity type, wherein said cathode region further comprises:
      an upper layer, which is arranged over the first buffer layer;
      a second buffer layer, which is arranged underneath the anode region and overlies, in direct contact, the upper layer, said second buffer layer having a doping level higher than a doping level of said upper layer.

5. The optoelectronic device according to claim 4, wherein:
   the first buried region is arranged between the lower layer and the first buffer layer, and directly contacts the lower layer and the first buffer layer; and
   said second buried region is arranged between the upper layer and the second buffer layer, and directly contacts the upper layer and the second buffer layer; said optoelectronic device further comprising:
   a first trench, which traverses the front surface and extends in the cathode region, said first trench traversing the first buffer layer and a portion of the first buried region;
   a first conductive region, which extends within the first trench and contacts the first buffer layer and the first buried region;
   a second trench, which traverses the front surface and extends in the cathode region, said second trench traversing the second buffer layer and a portion of the second buried region; and
   a second conductive region, which extends within the second trench and contacts the second buffer layer and the second buried region.

6. The optoelectronic device according to claim 4, further comprising:
   a first trench, which traverses the front surface and extends in the cathode region, said first trench including a top portion, which traverses the first buffer layer, and a bottom portion, which extends within the lower layer;

a first dielectric coating region, which coats side walls of the top portion of the first trench;

a first conductive region including a top portion, which extends within the top portion of the first trench, and is surrounded by the first dielectric coating region, and a respective bottom portion, which extends within the bottom portion of the first trench, wherein the first buried region surrounds laterally and underneath the bottom portion of the first conductive region, and directly contacts the bottom portion of the first conductive region;

a second trench, which traverses the front surface and extends in the cathode region, said second trench including a top portion, which traverses the second buffer layer, and a bottom portion, which extends within the upper layer;

a second dielectric coating region, which coats side walls of the top portion of the second trench; and a second conductive region including a respective top portion, which extends within the top portion of the second trench and is surrounded by the second dielectric coating region, and a respective bottom portion, which extends within the bottom portion of the second trench;

and wherein the second buried region surrounds laterally and underneath the bottom portion of the second conductive region, and directly contacts the bottom portion of the second conductive region.

7. An array comprising a plurality of optoelectronic devices for detecting radiation, each optoelectronic device including:

a cathode region formed in a semiconductor body, the cathode region being delimited by a front surface of the semiconductor body, and having a first conductivity type, said cathode region having a lower layer;

an anode region having a second conductivity type, which extends in the cathode region starting from the front surface and forms a shallow junction with said cathode region;

a first buried region having the second conductivity type, which extends within the cathode region and forms a first buried junction with said lower layer; wherein said cathode region further comprises a first buffer layer, which is arranged underneath the anode region and overlies, in direct contact, the lower layer, said first buffer layer having a doping level higher than a doping level of the lower layer;

a first trench, which traverses the front surface and extends in the cathode region, said first trench including a top portion, which traverses the first buffer layer, and a bottom portion, which extends within the lower layer;

a first dielectric coating region, which coats side walls of the top portion of the first trench; and a first conductive region including a top portion, which extends within the top portion of the first trench, and is surrounded by the first dielectric coating region, and a respective bottom portion, which extends within the bottom portion of the first trench; wherein the first buried region surrounds laterally and underneath the bottom portion of the first conductive region, and directly contacts the bottom portion of the first conductive region.

8. The array according to claim 7, wherein each optoelectronic device further includes a second buried region having the second conductivity type and the cathode region further comprises:

an upper layer, which is arranged over the first buffer layer; and a second buffer layer, which is arranged underneath the anode region and overlies, in direct contact, the upper layer, said second buffer layer having a doping level higher than a doping level of said upper layer.

9. A detection system comprising:

an optoelectronic device for detecting radiation, the optoelectronic device including:

a cathode region formed in a semiconductor body, the cathode region being delimited by a front surface of the semiconductor body and having a first conductivity type, said cathode region having a lower layer;

an anode region having a second conductivity type, which extends in the cathode region starting from the front surface and forms a shallow junction with said cathode region;

a first buried region having the second conductivity type, which extends within the cathode region and forms a first buried junction with said lower layer, wherein said cathode region further comprises a first buffer layer, which is arranged underneath the anode region and overlies, in direct contact, the lower layer, said first buffer layer having a doping level higher than a doping level of the lower layer;

a first trench, which traverses the front surface and extends in the cathode region, said first trench including a top portion, which traverses the first buffer layer, and a bottom portion, which extends within the lower layer;

a first dielectric coating region, which coats side walls of the top portion of the first trench; and a first conductive region including a top portion, which extends within the top portion of the first trench, and is surrounded by the first dielectric coating region, and a respective bottom portion, which extends within the bottom portion of the first trench; wherein the first buried region surrounds laterally and underneath the bottom portion of the first conductive region, and directly contacts the bottom portion of the first conductive region;

a power supply configured to bias by turns the shallow junction and the first buried junction; and an electronic circuit configured to determine a first quantity and a second quantity indicating, respectively, a light intensity of a first spectral component of the radiation and a light intensity of a second spectral component of the radiation.

10. The detection system according to claim 9, wherein:

said shallow junction is configured to generate, in response to the radiation that impinges on the front surface, a first current proportional to the light intensity of a first spectral component of said radiation; and said first buried junction is configured to generate a second current proportional to the light intensity of the second spectral component of said radiation.

11. A process for manufacturing an optoelectronic device for detecting radiation, comprising:

forming a cathode region in a semiconductor body, the cathode region being delimited by a front surface of the semiconductor body, having a first conductivity type, and including a lower layer;

inside the cathode region, forming, starting from the front surface, an anode region having a second conductivity type, the anode region forming a shallow junction with the cathode region;

inside the cathode region, forming a first buried region having the second conductivity type, the first buried region forming a first buried junction with the lower layer; wherein forming the cathode region further comprises forming, underneath the anode region, a first buffer layer that overlies, and directly contacts, the lower layer, said first buffer layer having a doping level higher than a doping level of the lower layer, and wherein forming the first buried region comprises forming the first buried region between, and in direct contact with, the lower layer and the first buffer layer;

forming a first trench that traverses the front surface, extends in the cathode region, and traverses the first buffer layer and a portion of the first buried region; and inside the first trench, forming a first conductive region that contacts the first buffer layer and the first buried region.

12. The manufacturing process according to claim 11, wherein:
the first trench includes a top portion, which traverses the first buffer layer, and a bottom portion, which extends within the lower layer;
the first conductive region includes a top portion inside the top portion of the first trench and a bottom portion inside the bottom portion of the first trench; and
forming the first buried region comprises forming the first buried region that surrounds laterally and underneath the bottom portion of the first conductive region, and directly contacts the first conductive region, the process further comprising:
forming a first dielectric coating region on side walls of the top portion of the first trench, wherein a top portion of the first conductive region is surrounded by the first dielectric coating region.

13. A manufacturing process for manufacturing an optoelectronic device for detecting radiation, comprising:
forming a cathode region in a semiconductor body, the cathode region being delimited by a front surface of the semiconductor body, having a first conductivity type, and including a lower layer;
inside the cathode region, forming, starting from the front surface, an anode region having a second conductivity type, the anode region forming a shallow junction with the cathode region;
inside the cathode region, forming a first buried region having the second conductivity type, the first buried region forming a first buried junction with the lower layer; wherein forming the cathode region further comprises forming, underneath the anode region, a first buffer layer that overlies, and directly contacts, the lower layer, said first buffer layer having a doping level higher than a doping level of the lower layer, wherein said forming the cathode region further comprises:
forming over the first buffer layer an upper layer; and
forming underneath the anode region a second buffer layer so that it overlies, in direct contact, the upper layer, said second buffer layer having a doping level higher than a doping level of said upper layer; and
forming a second buried region having the second conductivity type so that the second buried region forms a second buried junction with the upper layer.

14. The manufacturing process according to claim 13, wherein:
forming the first buried region comprises forming the first buried region between, and in direct contact with, the lower layer and the first buffer layer;

forming the second buried region comprises forming said second buried region arranged between, and in direct contact with, the upper layer and the second buffer layer; said process further comprising:
forming a first trench that traverses the front surface, extends in the cathode region, and traverses the first buffer layer and a portion of the first buried region;
inside the first trench, forming a first conductive region that contacts the first buffer layer and the first buried region;
forming a second trench that traverses the front surface, extends in the cathode region, and traverses the second buffer layer and a portion of the second buried region; and
inside the second trench, forming a second conductive region that contacts the second buffer layer and the second buried region.

15. The manufacturing process according to claim 13, further comprising:
forming a first trench that traverses the front surface, extends in the cathode region, and includes a top portion, which traverses the first buffer layer, and a bottom portion, which extends within the lower layer; and
forming a first dielectric coating region on side walls of the top portion of the first trench; and
inside the top portion of the first trench, forming a top portion of a first conductive region, the top portion being surrounded by the first dielectric coating region; and
inside the bottom portion of the first trench, forming a bottom portion of the first conductive region;
forming a second trench that traverses the front surface, extends in the cathode region, and includes a top portion, which traverses the second buffer layer, and a bottom portion, which extends within the upper layer;
forming a second dielectric coating region on side walls of the top portion of the second trench;
inside the top portion of the second trench, forming a top portion of a second conductive region, is the top portion of a second conductive region being surrounded by the second dielectric coating region; and
inside the bottom portion of the second trench, forming a bottom portion of the second conductive region; wherein:
said forming the first buried region comprises forming the first buried region that surrounds laterally and underneath the bottom portion of the first conductive region, and directly contacts the first conductive region; and
forming the second buried region comprises forming the second buried region that surrounds laterally and underneath the bottom portion of the second conductive region, and directly contacts the bottom portion of the second conductive region.

16. The manufacturing process according to claim 13, further comprising:
forming a first trench that traverses the front surface, extends in the cathode region, and includes a top portion, which traverses the first buffer layer, and a bottom portion, which extends within the lower layer, wherein said first trench has a ring shape;
forming first dielectric coating region on side walls of the top portion of the first trench, including forming an inner dielectric coating region and an outer dielectric coating region on the side walls of the first trench;

inside the top portion of the first trench, forming a top portion of a first conductive region, the top portion being surrounded by the first dielectric coating region; and inside the bottom portion of the first trench, forming a bottom portion of the first conductive region, wherein forming the inner and outer coating regions includes:

after forming the first trench, coating the side walls and the bottom of the first trench with at least one dielectric coating layer;

forming, on the at least one dielectric coating layer, a first protective layer and a second protective layer, which are opposite to one another and leave exposed a portion of said at least one dielectric coating layer that coats the bottom portion of the first trench;

selectively removing the exposed portion of said at least one dielectric coating layer and exposing an underlying portion of the bottom layer; and removing the first and second protective layers; wherein:
forming the top portion and the bottom portion of a first conductive region comprise forming in the first trench a first polysilicon region with the second doping type, the first polysilicon region contacting the inner coating region, the outer coating region, and the lower layer; and forming the first buried region comprises carrying out a thermal treatment that causes dopant impurities present in the first polysilicon region to diffuse into the lower layer.

17. The manufacturing process according to claim 16, further comprising forming a top dielectric region over the front surface; wherein forming the first trench comprises forming the first trench that traverses also the top dielectric region; and selectively removing a portion of the top dielectric region and exposing an underlying portion of the cathode region; and on the exposed underlying portion of the cathode region, forming a second polysilicon region with the second doping type; wherein carrying out said thermal treatment includes causing dopant impurities present in the second polysilicon region to diffuse into the cathode region.

18. A process for manufacturing an optoelectronic device for detecting radiation, comprising:

forming a cathode region in a semiconductor body, the cathode region being delimited by a front surface of the semiconductor body, having a first conductivity type, and including a lower layer;

inside the cathode region, forming, starting from the front surface, an anode region having a second conductivity type, the anode region forming a shallow junction with the cathode region;

inside the cathode region, forming a first buried region having the second conductivity type, the first buried region forming a first buried junction with the lower layer;

wherein forming the cathode region further comprises forming, underneath the anode region, a first buffer layer that overlies, and directly contacts, the lower layer, said first buffer layer having a doping level higher than a doping level of the lower layer;

forming a first trench that traverses the front surface, extends in the cathode region, and includes a top portion, which traverses the first buffer layer, and a bottom portion, which extends within the lower layer;

forming a first dielectric coating region on side walls of the top portion of the first trench;

inside the top portion of the first trench, forming a top portion of a first conductive region, the top portion being surrounded by the first dielectric coating region;

inside the bottom portion of the first trench, forming a bottom portion of the first conductive region; wherein forming the first buried region comprises forming the first buried region that surrounds laterally and underneath the bottom portion of the first conductive region, and directly contacts the first conductive region.

19. The manufacturing process according to claim 18, wherein forming the cathode region further comprises:

forming over the first buffer layer an upper layer; and
forming underneath the anode region a second buffer layer so that it overlies, in direct contact, the upper layer, said second buffer layer having a doping level higher than a doping level of said upper layer, the process further comprising:

forming a second buried region having the second conductivity type so that the second buried region forms a second buried junction with the upper layer.

* * * * *